United States Patent [19]

Lazarus et al.

[11] Patent Number: 5,227,469
[45] Date of Patent: Jul. 13, 1993

[54] PLATELET AGGREGATION INHIBITORS FROM THE LEECH

[75] Inventors: Robert A. Lazarus; Jana L. Seymour, both of South San Francisco, Calif.

[73] Assignee: Genentech, Inc., South San Francisco, Calif.

[21] Appl. No.: 602,847

[22] Filed: Oct. 26, 1990

Related U.S. Application Data

[63] Continuation-in-part of Ser. No. 479,829, Feb. 14, 1990.

[51] Int. Cl.$^5$ .............................................. C07K 7/10
[52] U.S. Cl. ..................................... 530/324; 530/326
[58] Field of Search ........................... 514/12, 21, 822; 530/320, 855; 435/69.1

[56] References Cited

U.S. PATENT DOCUMENTS 4,683,291  7/1987  Zimmerman et al. .............. 530/324

*Primary Examiner*—Robert A. Wax
*Assistant Examiner*—P. Schmickel
*Attorney, Agent, or Firm*—Daryl B. Winter

[57] ABSTRACT

A composition of matter derived from hematophagous leech comprising specified purified amino acid sequences represented by the general formula:

CXXXRGDXXXXC(Seq. ID No. 11)

and capable of functioning as an antithrombotic by inhibiting the binding of fibrinogen to the platelet glycoprotein II$_b$ III$_a$ (GP II$_b$ III$_a$), a fibrinogen receptor. Methods for the purification of amino acid sequences from leeches, and particularly from leeches of the genus Macrobdella and Placobdella. are provided. Isolated nucleic acid sequences encoding these amino acid sequences; an expression vector containing the isolated nucleic acid; and a cell containing the expression vector are also described. A process for chemical synthesis of the amino acid sequences and a method for reducing platelet aggregation in a mammal by administering a composition containing the amino acid sequences to the mammal in a pharmaceutically effective amount are provided.

3 Claims, 11 Drawing Sheets

```
                                    1           5          10         15
Decorsin                          A P R L P Q C V G D D Q E K C L C N Echistatin                                                 E C E S G P C C R N C
Trigramin     E A G E D C D C G S P A N P C C D A A T C K L I P G A Q C G E G L C C D Q C
Applaggin     E A G E E C D C E S P E N P C C D A A T C K L R P G A Q C A E G L C C D Q C
Kistrin       G K E C D C S S P E N P C C D A A T C K L R P G A Q C G E G L C C E Q C 20          25          30          35
Decorsin      K D E C P P G Q C R F P R G D A - D P Y C E Echistatin    K F L K E G T I C K R A R G D D M D D Y C N G K T C D C P R N P H K G P A T
Trigramin     S F I E E G T V C R I A R G D D L D D Y C N G R S A G C P R N P F H
Applaggin     K F M K E G T V C R - A R G D D V N D Y C N G I S A G C P R N P F H
Kistrin       K F S R A G K I C R I P R G D M P D D R C T G Q S A D C P R Y H
```

Fig.5.

```
       ecoRI                        sacII                        styI
    1 AATTC CCG GGA ATC GAA GGT CGT GCG CCG CTG CCG CAG TGC CAA GGT GAC GAT CAG GAA AAA TGT CTG TGC AAC AAA
      G GGC CCT TAG CTT CCA GCA CGC GGC GCC GAC GTC ACG GTT CCA CTG CTA GTC CTT TTT ACA GAC ACG TTG TTT
    1   Pro Gly Ile Glu Gly Arg Ala Pro Arg Leu Pro Gln Cys Gln Gly Asp Asp Gln Glu Lys Cys Leu Cys Asn Lys xhoI                                                    sphI        salI      xbaI
   81 GAT GAA TGT CCC CCG GGT CAG TGT CGT TTC CCT CGA GGT GAT GCG GAT CCG TAT TGT GAA TAA GCA TGC GTC GAC TCT AGA
      CTA CTT ACA GGG GGC CCA GTC ACA GCA AAG GGA GCT CCA CTA CGC CTA GGC ATA ACA CTT ATT CGT ACG CAG CTG AGA TCT
   26  Asp Glu Cys Pro Pro Gly Gln Cys Arg Phe Pro  Arg Gly Asp Ala Asp Pro Tyr Cys Glu OC* banIII[M.haeIII-]
       apaI      hindIII pstI
  162 GGG CCC AAA GCT TCT GCA
      CCC GGG TTT CGA AG
   53
```

Fig.6.

```
         narI
         haeII sacII              styI
    1  GCG CCG CGG CTG CCG CAG TGC CAA GGT GAC GAT GAA AAA TGT CTG TGC AAC AAA GAT GAA TGT CCC CCG GGT
       ACGT CGC GGC GCC GAC GGC GTC ACG GTT CCA CTG CTA GAC CTT TTT ACA GAC ACG TTG TTT CTA CTT ACA GGG GGC CCA
                                                                              ↑                          xmaI
                                                                           styI                          smaI
    1  Ala Pro Arg Leu Pro Gln Cys Gln Gly Asp Asp Glu Lys Cys Leu Cys Asn Lys Asp Glu Cys Pro Pro Gly
             ↓ xhoI                       bamHI                        styI
                                                                       blgII
   80  CAG TGT CGT TTC CCT CGA GGT GAT GCG GAT CCG TAT TGT GAA TAA A
       GTC ACA GCA AAG GGA GCT CCA CTA CGC CTA GGC ATA ACA CTT ATT TCTAG
                         ↑
   26  Gln Cys Arg Phe Pro Arg Gly Asp Ala Asp Pro Tyr Cys Glu OC*
```

| | |
|---|---|
| OrnatinA2 | IPQCRDVKESGQPNDKCRCNGKPCTVGKCTIARGDNDKCT |
| OrnatinB | IYVRPTNDELNYCGDFRELGQPDKKCRCDGKPCTVGRCKFARGDNDDKCISA |
| OrnatinC | IYVRPTKDELLYCGEFRELGQPDKKCRCDGKPCTVGRCKFARGDADDKCTSA |
| OrnatinD | IYVRPTKDELLYCGEFRELGQPDKKCRC |
| OrnatinE | IYVRPTKDELLYCGEFRELGQPDKKCRCDGKPCTVGRCNFARGDNDDKCI |
| Decorsin | APRLPQCQGDDQEKCLCNKDECPPGQCRFPRGDADPYCE |

```
            nsII         sstI
                         sacI
                         banII[M.aluI-]           nruI
  1   ATC TAT GTT CGT CCG ACC AAA GAT GAG CTC CTG TAT TGT GGT GAA TTT CGC GAA CTG GGT CAG CCG GAT AAA AAA
      ACGT TAG ATA CAA GCA GGC TGG TTT CTA CTC GAG GAC ATA ACA CCA CTT AAA GCG CTT GAC CCA GTC GGC CTA TTT TTT
  1   Ile Tyr Val Arg Pro Thr Lys Asp Glu Leu Leu Tyr Cys Gly Glu Phe Arg Glu Leu Gly Gln Pro Asp Lys Lys
                                                                              bssHII
 80   TGC CGT TGT GAT GGT AAA CCG TGT ACC GTT GGT CGT TGT AAC TTC GCG CGC GGT GAT AAC GAT GAT AAA TGT ATC TAA TGA
      ACG GCA ACA CTA CCA TTT GGC ACA TGG CAA CCA GCA ACA TTG AAG CGC GCG CCA CTA TTG CTA CTA TTT ACA TAG ATT ACT
 26   Cys Arg Cys Asp Gly Lys Pro Cys Thr Val Gly Arg Cys Asn Phe Ala Arg Gly Asp Asn Asp Asp Lys Cys Ile OC* sphI  xhoII
      nspI  bamHI styI
161   GCATGCGGAT CC
      CGTACGCCTA GGGAAC
```

Fig. 10.

PLATELET AGGREGATION INHIBITORS FROM THE LEECH

CROSS-REFERENCE TO RELATED APPLICATION

This is a continuation-in-part of prior co-pending application Ser. No. 479,829 filed Feb. 14, 1990.

FIELD OF THE INVENTION

The present invention is directed to inhibitors of platelet aggregation obtained form the leech. The invention includes methods for isolating the inhibitors from natural sources, synthesis of the inhibitors, genes encoding the inhibitors, expression of the genes, the gene products, and therapeutic applications of the inhibitors in diseases for which blocking intercellular adhesion mediated by the fibrinogen receptor is indicated.

More specifically, the present invention is directed to inhibitors which, by blocking the binding of fibrinogen to the platelet fibrinogen receptor, glycoprotein $IIb\,IIIa$, antagonize the final common pathway of platelet aggregation and act as potent antithrombotics.

BACKGROUND OF THE INVENTION

Platelet aggregation plays a fundamental role in the hemostatic response, and in thrombotic disease (Colman, R. W. and Walsh, P. N. (1987) in *Hemostasis and Thrombosis: Basic Principles and Clinical Practice*, Colman, R. W., Hirsch, J., Marder, V. J., and Salzman, E. W., eds. (J. B. Lippincott Company, Philadelphia), pp. 594–605; and Stein, B., Fuster, V., Israel, D. H., Cohen, M., Badimon, L., Badimon, J. J., and Chesebro, J. H. (1989) *J. Am. Coll. Cardiol.* 14, 813–836). It is believed that the first step in platelet aggregation involves activation of platelets, however, the mechanisms of platelet activation and subsequent aggregation are complex, characterized by numerous intracellular pathways and extracellular ligands and binding sites. It is known, however, that glycoprotein $IIb\,IIIa$ (GP $IIb\,IIIa$), a $Ca^{+2}$ dependent heterodimeric receptor (Phillips, D. R., Charo, I. F., Parise, L. V., and Fitzgerald, L. A. (1988) *Blood,* 71, 831–843; and Plow, E. F. and Ginsburg, M. H. (1989) in *Progress in Hemostasis and Thrombosis*, Coller, B. S., ed., (W. B. Saunders Company, Philadelphia), vol 9, pp. 117–156), when exposed on the surface membrane of activated platelets, can bind different adhesive proteins such as fibrinogen (Fg), fibronectin, von Willebrand factor, or vitronectin. The binding of fibrinogen to platelets via GP $IIb\,IIIa$ mediates aggregation and is critical to the formation of a hemostatic plug at an injured vessel wall. This interaction is considered to be the final common step of all platelet aggregation pathways and therefore provides an ideal target for therapeutic intervention in thrombotic disorders. The specific binding mechanism for the interaction of GP $IIb\,IIIa$ to its ligands is unknown; however, it is thought to be manifested through an Arg-Gly-Asp (RGD) sequence, an adhesion site recognition sequence (Ruoslahti, E. and Pierschbacher, M. D. (1987), *Science* 238, 491–497) common to the adhesive proteins that bind to GP $IIb\,IIIa$.

Fibrinogen contains two RGD sequences at $A\alpha 95$–$97$ and $A\alpha 572$–$574$ (Doolittle, R. F., Watt, K. W. K., Colltrell, B. A., Strong, D. D. and Riley, M. (1979) *Nature* 280, 464–468). A third region of fibrinogen, corresponding to residues 400–411 of the gamma chain carboxy terminus, has also been implicated in binding to GP $IIb\,IIIa$ (Kloczewiak, M., Timmons, S., Lukas, T. J., and Hawiger, J. (1984) *Biochemistry* 23, 1767–1774). Evidence for the involvement of both the RGD and gamma chain regions in binding with GP $IIb\,IIIa$ is largely derived from binding and inhibition data and from studies with synthetic RGD peptides (Gartner, T. K. and Bennett, J. S. (1985) *J. Biol. Chem.* 260, 11891–11894; Plow, E. F., Pierschbacher, M. D., Ruoslahti, E., Marguerie, G. A., and Ginsberg, M. H. (1985) *Proc. Nat. Acad. Sci. USA* 82, 8057–8061; Haverstick, D. M., Cowan, J. F., Yamada, K. M., and Santoro, S. (1985) *Blood* 66, 946–952; and D'Souza, S. E., Ginsberg, M. H., Lam, S.-C. T., and Plow, E. F. (1988) *J. Biol. Chem.* 263, 3943–3951) and gamma chain peptides (Kloczewiak, M., Timmons, S., Bednarek, M. A., Sakon, M., and Hawiger, J. (1989) *Biochemistry* 28, 2915–2919).

It is known that proteins containing the peptide sequence RGD may be recognized as binding ligands of a number of cell adhesion receptors other than GP $IIb\,IIIa$. These cell adhesion receptors comprise a family of heterodimeric protein receptors known as the integrins (Ginsberg, M. H., Loftus, J. C., and Plow, E. F. (1988) *Thrombosis and Haemostasis* 59, 1–6; and Hynes, R. O. (1988) *Cell* 48, 549–554). Among these receptors shown to bind RGD containing ligands are the vitronectin receptors (VnR) and the fibronectin receptors (FnR) (Pytela et al. (1985) *Proc. Natl. Acad. Sci., USA* 82, 5766–5770; Pytela et al. (1985) *Cell* 40, 191–198; and Sanchez-Madrid et al. (1983) *J. Exp. Med.* 158, 1785–1803). Furthermore, it is believed that other integrin receptors may be discovered which interact with RGD containing proteins. Thus, RGD containing therapeutics may antagonize a number of protein ligand-receptor interactions.

Many proteins affecting hemostasis have been purified and characterized from natural sources including both snake venoms and leeches. In view of the complexity of platelet aggregation, it is believed that the agents found in these natural sources mediate their hemostatic effects through a variety of mechanisms, which include fibrinolysis (Stocker, K. F. (1990) in *Medical Uses of Snake Venoms*, Stocker, K. F. ed., (CRC Press, Boca Raton), pp. 97–160; and Malinconico, S. M., Katz, J. B., and Budzynski, A. (1984) *J. Lab. Clin. Med.* 103, 44–58), the inhibition of thrombin (Markwardt F. (1988) in *Hemostasis and Animal Venoms*, H. Pirkle and F. G. Markland, Jr.,eds., (Marcel Dekker, New York), pp. 225–269) and factor Xa (Nutt, E., Gasic, T., Rodkey, J., Gasic, G. J., Jacobs, J. W. and Friedman, P. A. (1988) *J. Boil. Chem.* 263, 10162–10167; and Condra, C., Nutt, E., Petroski C. J., Simpson, E., Friedman, P. A., and Jacobs, J. W. (1989) *Thromb. Haemostas.* 61, 437–441), as well as antagonism of GP $IIb\,IIIa$ receptor binding to Fg (Huang, T. F., Holt, J. C., Kirby, E. P., and Niewiarowski, S. (1989) *Biochemistry* 28, 661–666; Gan, Z. R., Gould, R. J., Jacobs, J. W., Friedman, P. A., and Polokoff, M. A. (1988) *J. Biol. Chem.* 263, 19827–19832; Chao, B. H., Jakubowski, J. A., Savage, B., Chow, E. P., Marzec, U. L., Harker, L. A., and Maraganore, J. M. (1989) *Proc. Natl. Acad. Sci. USA* 86, 8050–8054; Shebuski, R. J. Ramjit, D. R. Bencen, G. H., and Polokoff, M. A. (1989) *J. Biol. Chem.* 264, 21550–21556; Dennis, M. S., Henzel, W. J., Pitti, R. M., Lipari, M. T., Napier, M. A., Deisher, T. A., Bunting, S. and Lazarus, R. A. (1990) *Proc. Natl. Acad. Sci. USA* 87, 2471–2475; Williams, J., Rucinski, B., Holt, J., and Niewiarowski, S. (1990) *Biochim. Biophys. Acta* 1039, 81–89; Musial, J., Niewiarowski, S., Rucinski, B., Stewart, G. J., Cook, J. J., Williams, J. A., and Edmunds Jr., L. H. (1990) *Circulation* 82, 261–273; and Seymour, J. L., Henzel, W. J., Nevins, B., Stults, J. T., and Lazarus, R. A. (1990) *J. Biol. Chem.* 265, 10143–10147).

Recent studies have established that the GP $II_b III_a$ receptor antagonists from the venoms of pit vipers, which all contain the RGD sequence, constitute a general class of homologous proteins that are potent inhibitors of platelet aggregation (Dennis, M. S., Henzel, W. J., Pitti, R. M., Lipari, M. T., Napier, M. A., Deisher, T. A., Bunting, S. and Lazarus, R. A. (1990) *Proc. Natl. Acad. Sci. USA* 87, 2471–2475; co-pending application U.S. Ser. No. 07/362,718, filed Jun. 7, 1989; Huang, T. F., Holt, J. C., Kirby, E. P., and Niewiarowski, S. (1989) *Biochemistry* 28, 661–666; Gan, Z. R., Gould, R. J., Jacobs, J. W., Friedman, P. A., and Polokoff, M. A. (1988) *J. Biol. Chem.* 263, 19827–19832; and Chao, B. H., Jakubowski, J. A., Savage, B., Chow, E. P., Marzec, U. L., Harker, L. A., and Maraganore, J. M. (1989 *Proc. Natl. Acad. Sci., USA* 86, 8050–8054). These venom proteins are highly homologous to one another and constitute a family of related proteins that interact directly with GP $II_b III_a$, thereby blocking Fg binding (co-pending application U.S. Ser. No. 07/362,718, filed Jun. 7, 1989).

Leeches have long been known to possess agents that affect hemostasis (Sawyer, R. T. (1986) *Leech Biology and Behaviour*, Clarendon Press, Oxford, 2, 467–523; Sawyer, R. T. (1988) *Hemostasis and Animal Vemons*, H. Pirkle and F. G. Markland, Jr., eds., Marcel Dekker, New York, pp. 271–279) and several proteins have been isolated from leeches that affect hemostasis by various mechanisms. These include hirudin, a thrombin inhibitor from *Hirudo medicinalis* (Markwardt, F., (1988) *Hemostasis and Animal Venoms*, H. Pirkle and F. G. Markland, Jr., eds., Marcel Dekker, New York, pp. 255–269; Dodt, J., Seemuller, U., maschler, R., and Fritz, H. (1985) *Biol. Chem. Hoppe-Seyler* 366, 379–385); antistasin, a factor Xa inhibitor from *Haementaria officinalis* (Nutt, E., Gasic, T., Todkey, J., Gasic, G. J., Jacobs, J. W. and Friedman, P. A. (1988) *J. Biol. Chem.* 263, 10162–10167); as well as a similar factor Xa inhibitor from *Haementaria ghilianii* (Condra, C., Nutt, E., Petroski, C. J., Simpson, E., Friedman, P. A., and Jacobs, J. W. (1989) *Thromb. Haemostas.* 61, 437–441); and hementin, a fibrinolytic enzyme from *Haementaria ghilianii* (Malinconico, S. M., Katz, J. B., and Budzynski, A. (1984) *J. Lab. Clin. Med.* 103, 44–58).

More recently, it has been reported that leeches, and in particular the saliva of the medicinal leech, *Hirudo medicinalis*, have active factors that are able to inhibit platelet aggregation (Rigbi M., Levy, H., Eldor, A., Iraqu, F., Teitelbaum, Orevi, M., Horovitz, A., and Galun, R. (1987) *Comp. Biochem. Physiol.* 88C, 95–98); other leeches were also found to possess platelet aggregation inhibitors. In one instance, the platelet aggregation inhibitor was found to be a collagenase of molecular weight 50,000 (Sawyer, R. T., et al., International Patent Application No. PCT/GB86/00481). This collagenase has also been identified in a wide variety of leeches.

Although inhibitors of platelet aggregation isolated from leeches have been reported previously (e.g., Sawyer, R. T., et al., International Patent Application No. PCT/GB 86/00481; Rigbi M., Levy, H., Eldor, A., Iraqu, F., Teitelbaum, Orevi, M., Horovitz, A., and Galun, R. (1987) *Comp. Biochem. Physiol.* 88C, 95–98), these inhibitors act at other, or unknown, points in the aggregation pathways. Prior to the present invention, there are no known reports of inhibitors of platelet aggregation which acit via antagonism of the GP $II_b III_a$ receptor that have been isolated from leeches. Thus, the present discovery represents the first description of GP $II_b III_a$ antagonists isolated from leeches that act as platelet aggregation inhibitors.

The recognition, isolation, and characterization of anticoagulant factors in leeches is complicated by the difficulties of obtaining sufficient raw material for study. These difficulties are compounded by the extreme complexity of the clotting system. While it is not necessary for purposes of the present application to detail the multiple biochemical pathways that constitute the clotting process, a large number of extrinsic and intrinsic factors, some contributing to more than one pathway, are involved and are not fully understood. The multiplicity of elements contributing to clotting, and the consequent number of possible interactions and feedback loops, makes it extremely difficult to accurately assess the effects and mechanism of an exogenously added agent. Potential targets for inhibition of platelet aggregation, include; phospholipase $A_2$, fibrinogen, thrombin, adenylate cyclase, cyclooxygenase, thromboxane synthase or receptor, and GP $II_b III_a$. There has been considerable recent interest in the GP $II_b III_a$ receptor, the most thoroughly studied member of the integrin family of cell adhesion receptors. Since many thrombotic diseases may be mediated by platelet adhesion and aggregation, Inhibitors of the Fg/GP $II_b III_a$ interaction have great potential as agents for therapeutic intervention in thrombotic disease (Stein, B., et al., (1989) *J. Am. Coll. Cardiol.* 14, 813–836).

Therefore, it is an object of the present invention to ascertain whether hematophagous leeches contain antithrombotic agents that act via inhibition of GP $II_b III_a$/Fg binding to inhibit platelet aggregation. To achieve the foregoing object, it is a further object to develop a specific assay to measure the inhibition of GP $II_b III_a$/Fg binding, as well as an assay to detect inhibition of in vitro platelet aggregation.

It is still a further object to isolate and purify novel antithrombotic agents from leeches, especially those that inhibit Fg binding to GP $II_b III_a$. Additionally, it is an object to provide synthetic methods for producing leech derived antithrombotics for therapeutic intervention. These and other objects will be apparent from consideration of this application as a whole.

SUMMARY OF THE INVENTION

By means of the present invention the objectives described above have been realized, and there is accordingly provided herein a composition of matter comprising a purified amino acid sequence having at least about 70% homology with the sequences selected from:

RFPRGDADPY (Seq. ID No. 1),

TIARGDDNDK (Seq. ID No. 2),

KFARGDNDDK (Seq. ID No. 3),

KFARGDADDK (Seq. ID No. 4), and

NFARGDNDDK (Seq. ID No. 5).

This homology may include the sequence RGD. The preferred sequence may comprise sequences selected from the group:

PPGQCRFPRGDADPY (Seq. ID No. 6),

TVGKCTIARGDDNDK (Seq. ID No. 7),

TVGRCKFARGDNDDK (Seq. ID No. 8),

TVGRCKFARGDADDK (Seq. ID No. 9), and

TVGRCNFARGDNDDK (Seq. ID No. 10).

The composition may consist essentially of any one or more of these sequences.

In a more general embodiment of the invention, the purified amino acid sequence may be selected from the group:

CXXXRGDXXXXC (Seq. ID No. 11),

CXXXXCXXXRGDXXXXC (Seq. ID No. 12),

CXXXXCXXXXCXXXRGDXXXXC (Seq. ID No. 13),

CXCXXXXCXXXXCXXXRGDXXXXC (Seq. ID No. 14),

CXXXXXXXCXCXXXXCXXXXCXXXRGDXXXXC (Seq. ID No. 15),

CXXARGDXDDKC (Seq. ID No. 28),

CXXPRGDXDDKC (Seq. ID No. 29),

CTVGXCXXARGDXDDKC (Seq. ID No. 30),

CTVGXCXXPRGDXDDKC (Seq. ID No. 31), and mixtures thereof, where X is any amino acid, preferably a naturally occurring α-amino acid. The cysteines in this embodiment may be either reduced, or oxidized as disulfides.

For purposes of the present specification, applicants have provided the name "decorsin" (Seq. ID No. 16) for the 39-amino acid sequence:

APRLPQCQGDDQEKCLCNK-
DECPPGQCRFPRGDADPYCE, which is a full, native sequence corresponding to the purified amino acid sequence of the present invention. Numerous variations of this sequence, in terms of changes, deletions, and additions of amino acids, are possible without departing from the scope of the present invention. Thus, the purified amino acid sequence of the present invention extends to decorsin, isoforms of decorsin, analogs of decorsin, homologs of decorsin, and mixtures thereof.

Also for purposes of the present specification, applicants have provided the name "ornatin" for the isoforms of a protein isolated from *P. ornata* having the following amino acid sequences (Seq. ID Nos. 17, 18, 19, 20 and 21, respectively):

ornatinA2
IPQCRDVKESGQPNDKCRCNGKPCTVGK-
CTIARGDDNDKCT, ornatinB
IYVRPTNDELNYCGD-
FRELGQPDKKCRCDGKPCTVGRC-
KFARGDNDDKCISA, ornatinC
IYVRPTKDELLYCGE-
FRELGQPDKKCRCDGKPCTVGRC-
KFARGDADDKCTSA, ornatinD
IYVRPTKDELLYCGEFRELGQPDKKCRC,
and ornatinE
IYVRPTKDELLYCGE-
FRELGQPDKKCRCDGKPCTVGRCN-
FARGDNDDKCI.

These sequences represent the full, native sequences corresponding to the purified amino acid sequences of the present invention, with the exception of ornatinD which has only a partial sequence corresponding to the amino terminus of the protein.

As described above for decorsin, the present invention extends to various isoforms, analogs, homologs of ornatin, and mixtures thereof. Preferably, the compositions are sufficiently pure to yield a single major band on SDS-PAGE analysis using silver staining.

The composition of matter of the present invention may be an inhibitor of platelet aggregation and may act by inhibiting the binding of fibrinogen to platelets. This inhibition may occur via binding of the purified amino acid sequence to the GP $II_b III_a$ receptor.

The composition is preferably of sufficient purity such that the inhibition yields an $IC_{50}$ of no more than about 5 nM in a GP $II_b III_a$/Fg ELISA binding assay. Alternatively, the purity may be such that the composition substantially completely inhibits human platelet aggregation at a concentration of no more than about 1 μM in an assay for inhibition of ADP-induced platelet aggregation in human platelet rich plasma. More preferably, the composition is sufficiently pure to yield an $IC_{50}$ of no more than about 500 nM in the ADP-induced platelet aggregation assay.

The composition is preferably derived from hematophagous leech, and more preferably from the genera *Macrobdella decora*, Placobdella, Hirudo, Haemopis, and mixtures thereof. Still more preferably, the leech is selected from the species *Macrobdella decora, Placobdella ornata, Hirudo medicinalis, Haemopis grandis*, and mixtures thereof.

The composition may be made by purifying the inhibitors from leech ingestate, or crude homogenate of leeches, which may be derived from leeches selected from the genera and species listed above, as well as mixtures of the same.

The present invention further encompasses a composition of matter which comprises an inhibitor of GP $II_b III_a$/Fg binding derived from leech. The inhibitor is preferably a peptide, and more preferably a protein. The inhibitor may additionally be an inhibitor of platelet aggregation.

In a further embodiment, the present invention encompasses a composition of matter comprising isolated nucleic acid encoding the protein component of an amino acid sequence having at least about 70% homology with a sequence selected from the group:

RFPRGDADPY,

TIARGDDNDK,

KFARGDNDDK,

KFARGDADDK,

NFARGDNDDK,

PPGQCRFPRGDADPY,

TVGKCTIARGDDNDK,

TVGRCKFARGDNDDK,

TVGRCKFARGDADDK,

TVGRCNFARGDNDDK,

APRLPQCQGDDQEKCLCNK-
DECPPGQCRFPRGDADPYCE,

IPQCRDVKESGQPNDKCRCNGKPCTVGK-
CTIARGDDNDKCT,

IYVRPTNDELNYCGD-
FRELGQPDKKCRCDGKPCTVGRC-
KFARGDNDDKCISA,

IYVRPTKDELLYCGE-
FRELGQPDKKCRCDGKPCTVGRC-
KFARGDADDKCTSA,

IYVRPTKDELLYCGE-
FRELGQPDKKCRCDGKPCTVGRCN-
FARGDNDDKCI, and mixtures thereof (Seq. ID Nos. 1-10 and 16-21, respectively).

The composition of the present invention may be made by a process which includes the steps of isolating or synthesizing nucleic acid sequences encoding any of the amino acid sequences described above, ligating the nucleic acid sequence into a suitable expression vector capable of expressing the nucleic acid sequence in a suitable host, transforming the host with the expression vector into which the nucleic acid sequence has been ligated, culturing the host under conditions suitable for expression of the nucleic acid sequence, whereby the selected nucleic acid sequence is expressed by the host.

The present invention extends not only to the composition made by this process, but also to the process itself. In this process, the ligating step may further contemplate ligating the nucleic acid into a suitable expression vector such that the nucleic acid is operably linked to a suitable secretory signal, whereby the amino acid sequence is secreted by the host. The secretory signal may be selected from the group consisting of the leader of herpes gD, stII, lpp, alkaline phosphatase, invertase, and alpha factor, and is preferably stII.

The composition may be expressed as a fusion protein, that may include a protein selected from the group consisting of protein A, the Z domain of protein A, β-galactosidase, TrpE, che Y, streptavidin, protein G, CAT, polyglutamate, and polyhistidine. Preferably, the fusion protein is protein A or the Z domain of protein A.

In another embodiment, the present invention extends to an expression vector comprising the isolated nucleic acid. The expression vector may be selected from the group consisting of pBR322, pBO475, pRIT5, pRIT2T, pKK233-2, pDR540, and pPL-lambda.

The invention is further directed to a cell containing the expression vector. The cell may be eukaryotic, such as: African green monkey kidney cells (VERO-76, ATCC CRL-1587), human cervical carcinoma cells (HeLa, ATCC CCL-2), Chinese hamster ovary cells (CHO, Urlab and Chasin, Proc. Natl. Acad. Sci. USA, 77:4216 [1980]), human lung cells (W138, ATCC CCL-75), human embryonic kidney cell line 293 (Graham et al., J. Gen. Virol., 36:59 [1977]), baby hamster kidney cells (BHK, ATCC CCL-10), monkey kidney CVI line transformed by SV-40 (COS-7, ATCC CRL-1651) and canine kidney cells (MDCK, ATCC CCL-34) and the preferred eukaryotic cells are CHO and 293. The cell may alternatively be prokaryotic, such as E. coli K12 strain 294 (ATCC No. 31446), E. coli strain JM101, E. coli B, E. coli X1776 (ATCC No. 31537), E. coli c600, E. coli W3110 (F-, gamma-, prototrophic, ATCC No. 27325), Bacillus subtilis, Salmonella typhimurium, Serratia marcesans, and Pseudomonas species, with the preferred prokaryotic cell being E. coli W3110 (ATCC No. 27325).

The present invention further extends to therapeutic applications for the platelet aggregation inhibitor composition described herein. Those applications include, for example, a method for reducing platelet aggregation in a mammal, comprising administering a pharmaceutically effective amount of a composition of matter comprising the purified amino acid sequences described above to the mammal. The pharmaceutically effective amount may be between about 0.001 nM and 1.0 mM, is preferably between about 0.1 nM and 100 $\mu$M, and is most preferably between about 1.0 nM and 50 $\mu$M. The composition may be administered in admixture with a pharmacologically acceptable adjuvant. Additionally, the composition may be administered prior to, following, or simultaniously with administration of a fibrinolytic agent such as tissue plasminogen activator, streptokinase, urokinase, prourokinase, and modifications thereof.

An additional therapeutic application relates to a method for treating a mammal whose blood has an increased propensity for clotting. This method involves administering a pharmaceutically effective amount of a composition which includes a purified amino acid sequence which is an inhibitor of platelet aggregation, as provided by the present invention, to the mammal. The composition may further include a pharmacologically acceptable adjuvant.

The present invention further extends to compositions of matter for reducing platelet aggregation in a mammal, for treating a mammal whose blood has an increased propensity for clotting, and for inhibiting platelet aggregation in a mammal. These compositions each include a purified amino acid sequence which is an inhibitor of platelet aggregation, as described herein.

Finally, the composition of matter according to the present invention may directly inhibit the binding of fibrinogen to the GP II$_b$ III$_a$ receptor in a mammal. In this embodiment, the composition includes a purified amino acid sequence which binds to the GP II$_b$ III$_a$ receptor, also as described herein.

BRIEF DESCRIPTION OF FIGURES

FIG. 2: Separation of decorsin (A) and N-3 decorsin (B) using C18 rp HPLC. A Vydac C18 (5 $\mu$m, 4.6×250 mm) column was equilibrated in 15% acetonitrile containing 0.1% TFA. Decorsin and N-3 decorsin were eluted with a linear acetonitrile gradient (15 to 25%, 0.3% per minute) at a flow rate of 1 ml per minute. The gradient was started at the arrow and is illustrated with a dashed line; the absorbance at 214 nm is represented by the solid line.

Figure 3:
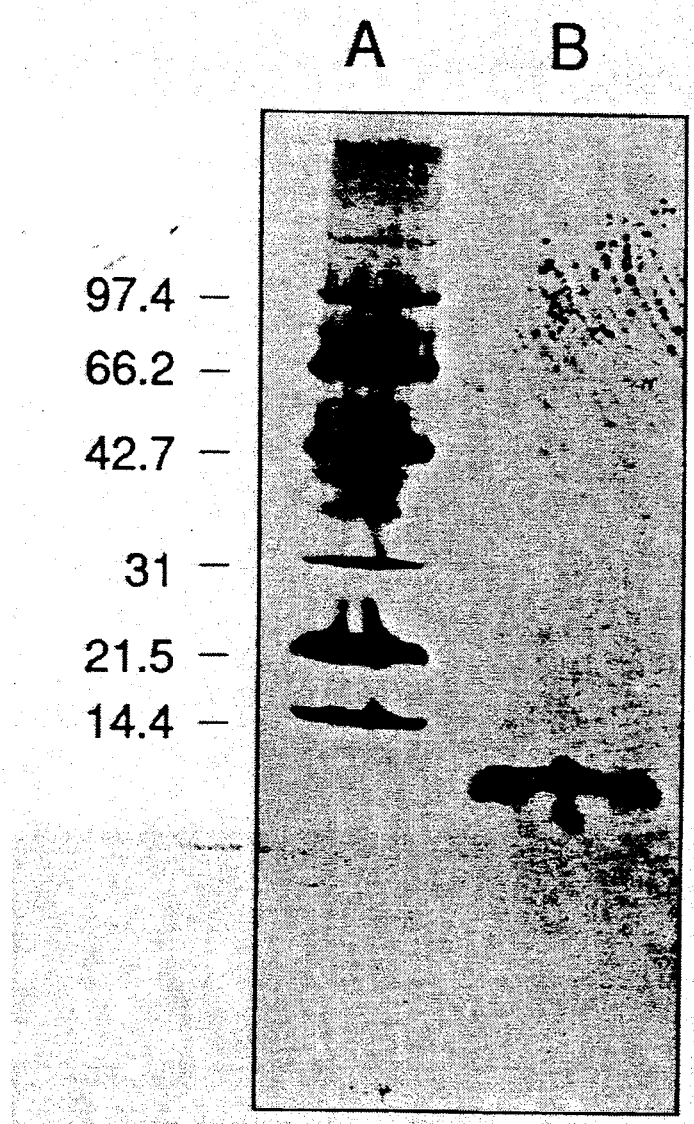

FIG. 3: SDS-polyacrylamide gel electrophoresis of purified decorsin. Purified decorsin (Lane B) and molecular mass standards (Lane A; molecular mass indicated in kilodaltons) were electrophoresed on a 8 to 25% polyacrylamide SDS PhastGel (Pharmacia). Proteins were reduced with dithiothreitol prior to electrophoresis and were visualized after electrophoresis by silver staining.

Figure 4:
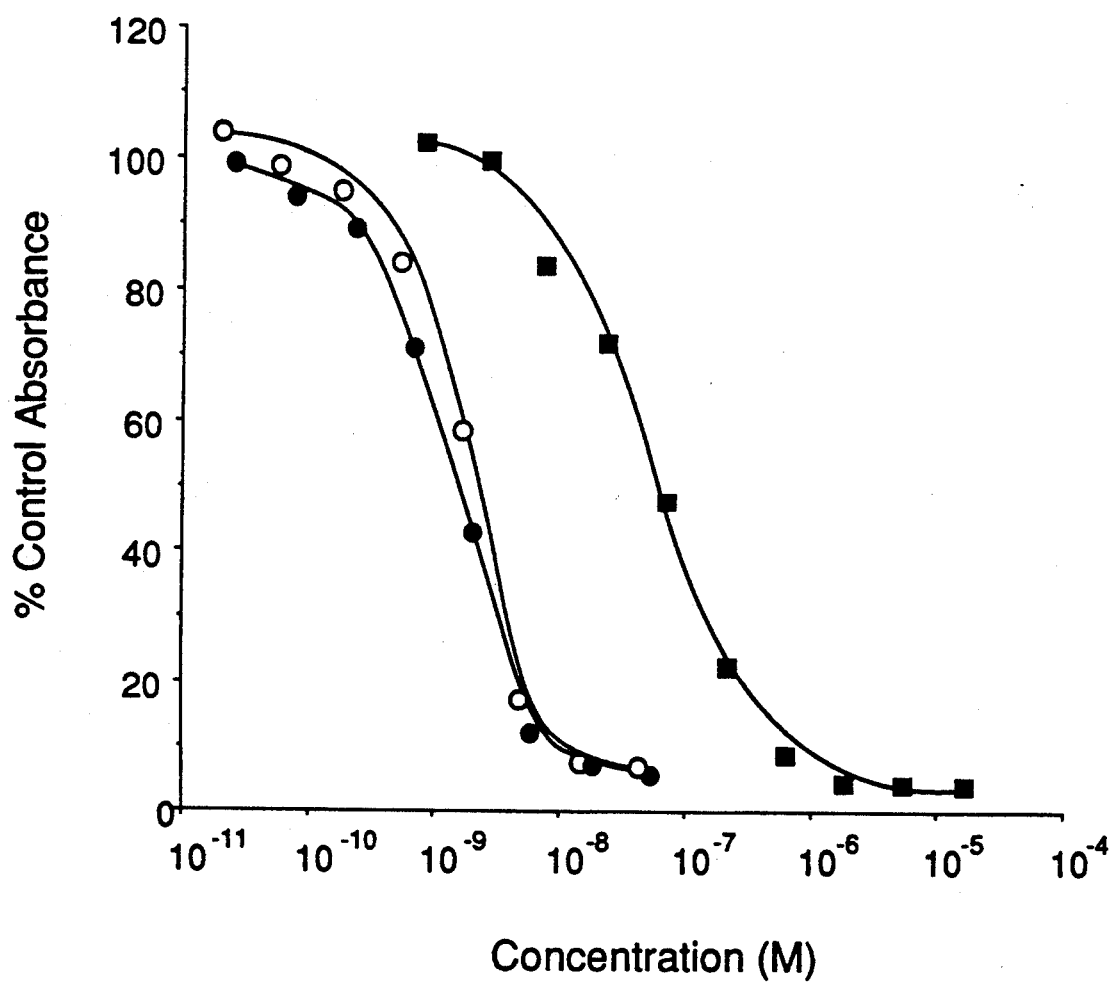

FIG. 4: Inhibition of GP $II_b III_a$ binding to immobilized fibrinogen by decorsin and N-3 decorsin. Inhibition of Fg/GP $II_b III_a$ binding was measured by a solid phase ELISA assay as described herein. Samples (decorsin ● — ●, N-3 decorsin ○ — ○, and GRGDV, ■ — ■) were serially diluted 1:3 with TACTS buffer and added to the Fg coated microtiter wells immediately preceding the addition of GP $II_b III_a$. Protein concentrations of the undiluted samples were determined by amino acid analysis. The concentration is shown plotted on a log scale, with the absorbance expressed as percent absorbance relative to wells containing only TACTS buffer and GP $II_b III_a$.

FIG. 5: Amino acid sequence comparison between decorsin and snake venom GP $II_b III_a$ antagonists. The sequence of decorsin is compared with echistatin (Gan, Z. R. et al. (1988) *J. Biol. Chem.* 263, 19827–19832); trigramin (Huang, T. F. et al. (1989) *Biochemistry* 28, 661–666); applaggin (Chao, B. H. et al. (1989) *Proc. Natl. Acad. Sci. USA* 86, 8050–8054); and kistrin (Dennis, M. S. et al., ibid.). These proteins are members of the snake venom family of GP $II_b III_a$ antagonists (Dennis, M. S. et al., ibid.). Areas of $\geq 50\%$ identity within the snake venom family and decorsin are shaded; the homologous RGD-containing region is boxed. The two positions (26 and 44) in the snake venom family where identity is 50% for each amino acid are unshaded. A gap was inserted into the decorsin and applaggin sequences to maximize homology.

FIG. 6: Provides a sequence of a fusion cassette for expression of decorsin fusion proteins. Synthetic oligonucleotides used to make the gene are indicated by the arrows and lines. Restriction sites are noted above the sequence.

FIG. 7: Provides a sequence of a cassette for direct expression of decorsin. Synthetic oligonucleotides used to make the gene are indicated by the arrows and lines. Restriction sites are noted above the sequence.

Figure 8:
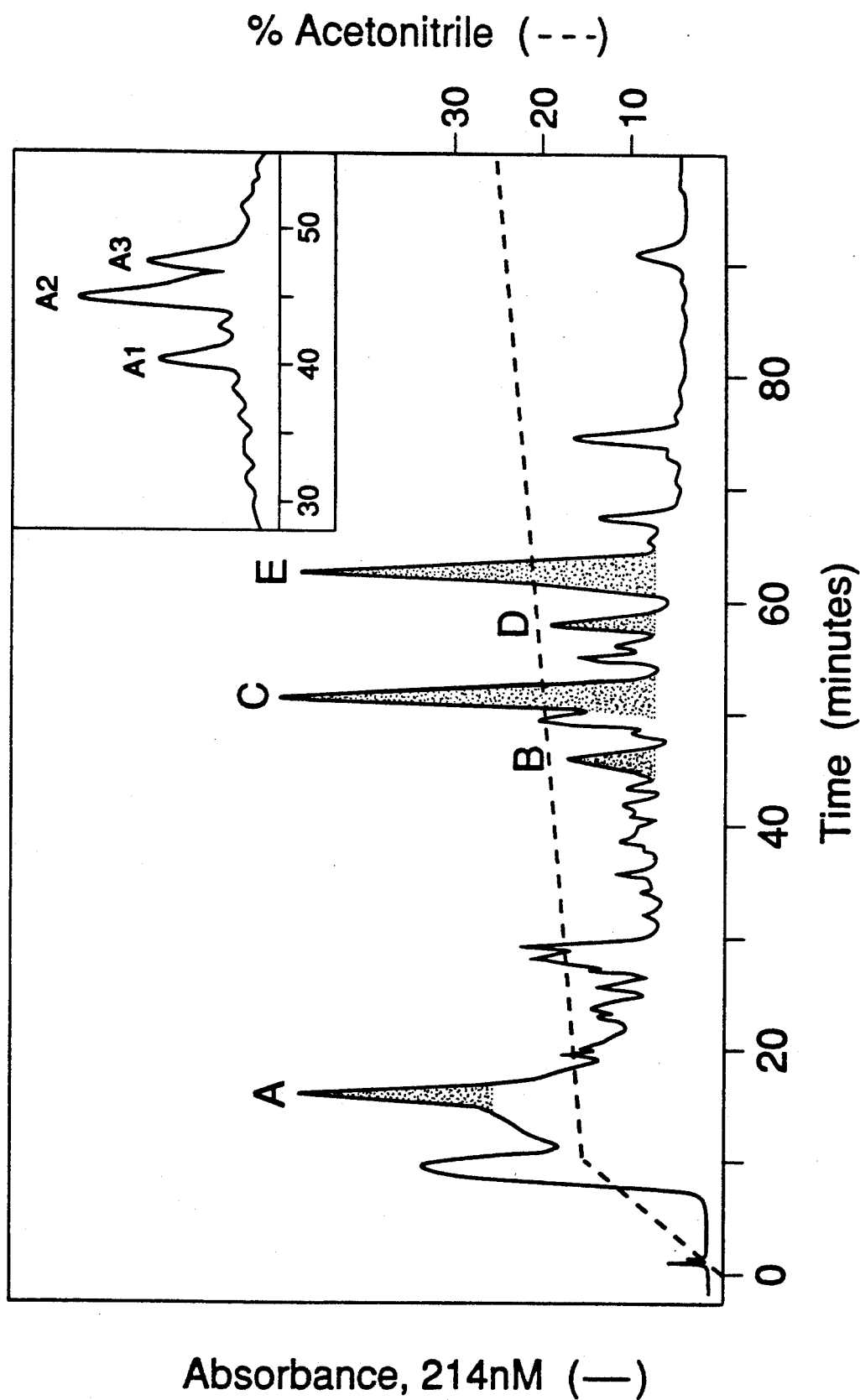

FIG. 8: Separation of ornatin isoforms by C18 rp HPLC into ornatin A, B, C, D and E. The inset shows further resolution of ornatin A into ornatin A1, A2 and A3. The shaded areas represent the most active peaks; peaks A1, A2, and A3 were also active.

FIG. 9: Amino acid sequences of ornatin isoforms and decorsin. The sequence for ornatin D represents a partial sequence. The RGD region is underlined and the cysteines are in boldface.

FIG. 10: The synthetic gene (ornE) designed to encode ornatinE. Synthetic oligonucleotides used to make the gene are indicated by the arrows and lines. Restriction sites are noted above the sequence.

Figure 11:
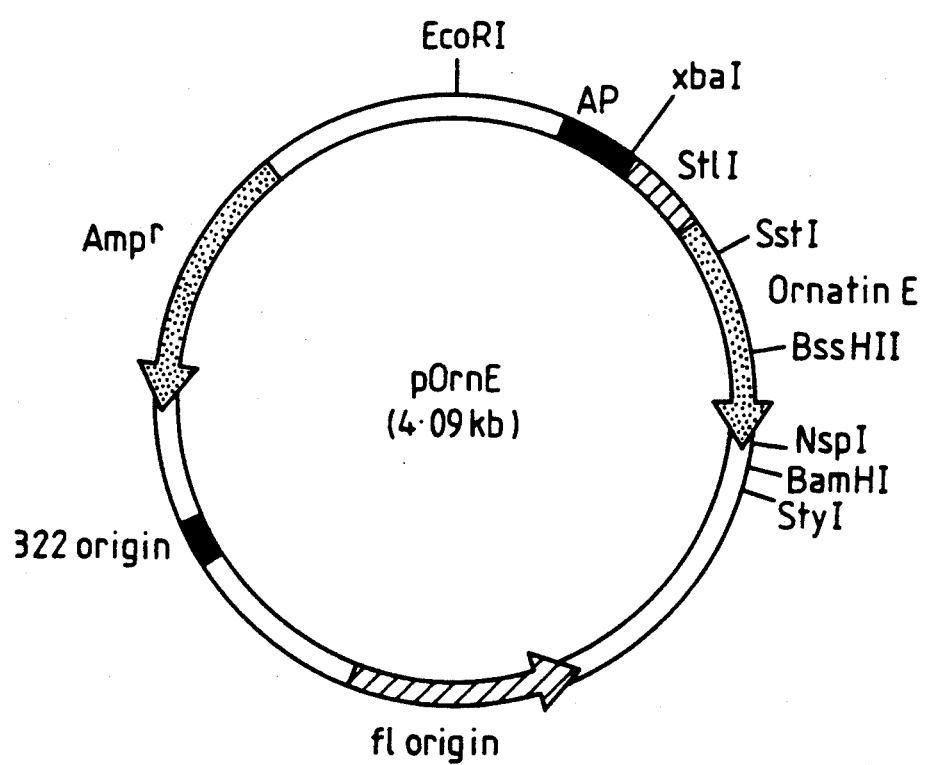

FIG. 11: Plasmid diagram of pOrnE, designed for secretion of ornatinE into the periplasm of *E. coli*. Genes and replication origins are indicated by arrows; important restriction sites are also noted.

DETAILED DESCRIPTION OF THE INVENTION

Figure 1:
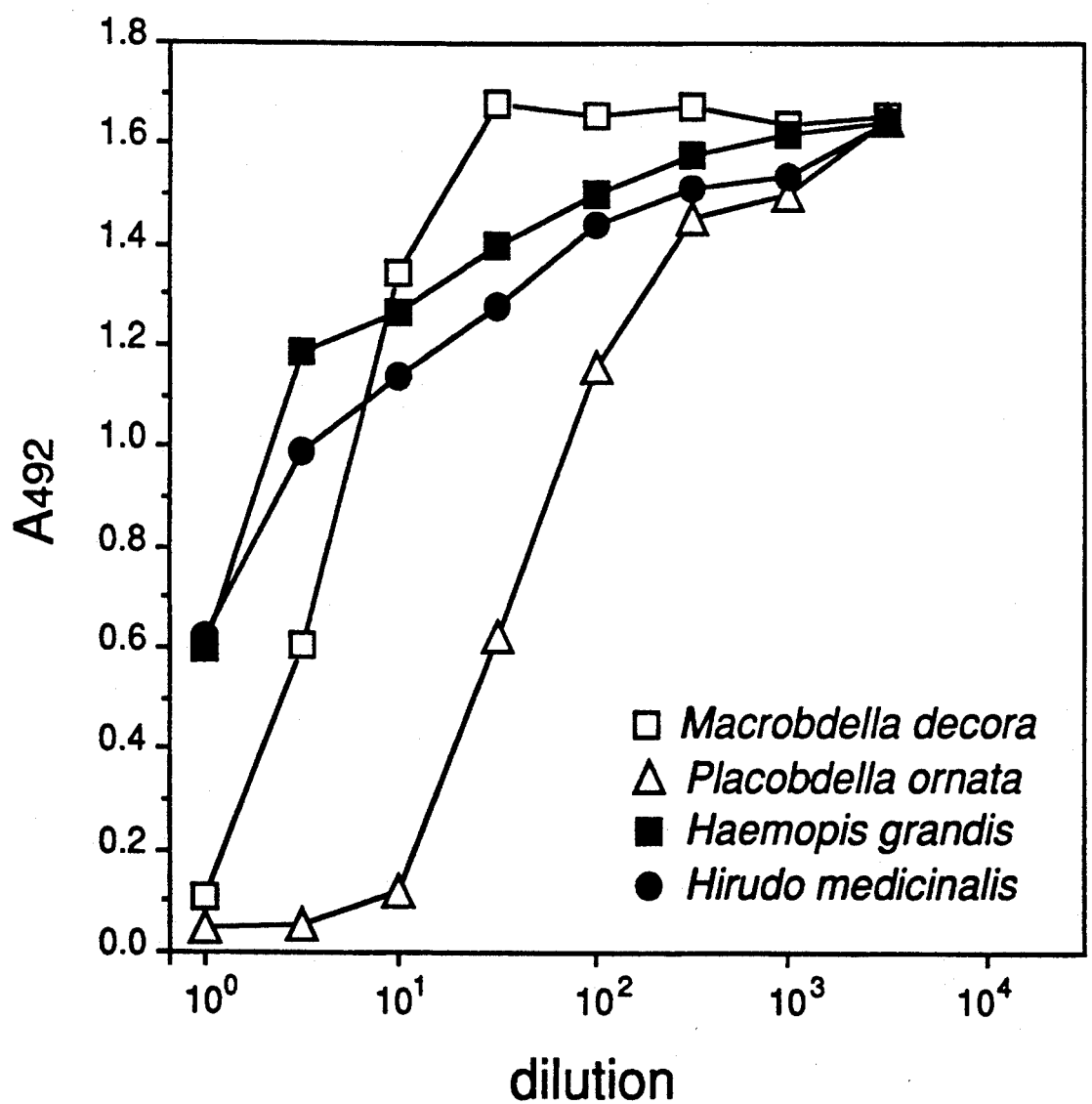
FIG. 1: Dose-dependent inhibition of Fg/GP II$_b$III$_a$ binding by supernatants of crude homogenates of Macrobdella decora, Placobdella ornata, Hirudo medicinalis, and Haemopis grandis, as measured by solid phase ELISA.

In the course of screening various crude leech homogenates in a Fg/GP $II_b III_a$ ELISA, inhibitory activity was detected in several homogenates including those from *Macrobdella decora* and *Placobdella ornata* (see FIG. 1).

This discovery led to the purification and characterization of a protein from *M. decora* which we have named decorsin. Decorsin acts as an antagonist of platelet glycoprotein $II_b III_a$ (GP $II_b III_a$), and is a potent inhibitor of platelet aggregation.

Decorsin has been isolated and purified to apparent homogeneity, both from whole leech homogenate and from leech salivary extract. Decorsin is 39 amino acids long (Table I), includes the sequence RGD, contains 6 cysteine and 6 proline residues, and has three disulfide bonds in its native (i.e., unreduced) form. Based on SDS-PAGE analysis, decorsin has an apparent molecular weight of <14.4 kD; the calculated molecular weight of the reduced protein is 4384 daltons.

Decorsin has been shown to bind to the GP $II_b III_a$ receptor using immobilized GP $II_b III_a$ affinity resin, and has an $IC_{50}$ of approximately 1.5 nM as measured by a GP $II_b III_a$/Fg ELISA. This is about 27 times more potent than the pentapeptide GRGDV (Seq. ID No. 34) ($IC_{50}$=about 40 nM).

In the platelet aggregation assay, decorsin effected complete inhibition as 1 μM, and has an $IC_{50}$ of approximately 300 nM. Comparable activities can be measured for the decorsin N-3 isoform, which lacks the first three amino terminal residues of decorsin.

The primary sequence of decorsin (Seq. ID No. 16) is:

APRLPQCQGDDQEKCLCNK-
DECPPGQCRFPRGDADPYCE and based on this sequence and composition, methodologies are described for the production of decorsin and its isoforms by chemical synthesis, as well as by recombinant DNA techniques.

This discovery also led to the identification, purification, and characterization of five isoforms of a protein from *P. ornata*, which we have named ornatin, that potently inhibit platelet aggregation through antagonism of GP $II_b III_a$/Fg binding. The primary sequences of these ornatins reveal that they are also cysteine rich RGD-containing proteins of considerable homology to each other. However, ornatin is quite distinct from either decorsin or the snake venom family of inhibitors, exhibiting homology only in the location of the cysteines and in the RGD region of the proteins.

Without being bound to any particular interpretation, theory, or explanation, the various results described herein support certain observations. Interestingly, we have found that all isoforms of these RGD containing leech derived Fg/GP $II_b III_a$ inhibitors have their RGD sequence flanked by two cysteines separated by exactly 10 amino acid residues (including RGD). Furthermore, the RGD sequence is positioned in precisely the same register relative to the cysteines, with three amino acid residues proceeding and four amino acids following the RGD sequence. Accordingly, for all isoforms tested so far, leech RGD containing Fg/GP $II_b III_a$ inhibitors comprise a sequence that can be represented by the following general formula:

CXXXRGDXXXXC (Seq. ID No. 11)

where X represents any amino acid.

This is in contradistinction to snake RGD containing Fg/GP II$_b$ III$_a$ venom inhibitors which comprise a sequence represented by the general formula CXXXRGDXXXXXC (Seq. ID No. 33)

where X represents any amino acid. Among snakes, this generic sequence is conserved in the venoms of various vipers (see e.g., WO-338 634, assigned to Merck; Dennis et. al., ibid.). The only deviation from this generic sequence for snakes thus far observed is applaggin in which one amino acid preceding the RGD sequence is deleted.

It is also interesting to note other differences observed upon comparison of the primary sequence of leech GP II$_b$ III$_a$ antagonists and some of the known snake venom GP II$_b$ III$_a$ antagonists (FIG. 5). Based on primary sequences, decorsin and ornatin do not appear to belong to the same family of GP II$_b$ III$_a$ protein antagonists that are found in snake venoms (Dennis et al.; Huang et al.; Gan et al.; and Chao et al.). However, the carboxy termini of both leech and snake platelet aggregation inhibitors contain the RGD sequence implying that this epitope is critical for tight binding to GP II$_b$ III$_a$.

It may prove that it is the presentation of this epitope that is important for the high affinity of these proteins to GP II$_b$ III$_a$. It is well-known that simple RGD containing peptides are able to inhibit platelet aggregation by interaction with GP II$_b$ III$_a$ (Gartner, T. K. and Bennett, J. S. (1985) *J. Biol. Chem.* 260, 11891-11894; Plow E. F., Pierschbacher, M. D., Ruoslahti, E., Marguerie, G. A., and Ginsberg, M. H. (1985) *Proc. Natl. Acad. Sci. USA* 82, 8057-8061). The higher affinity observed for both decorsin and the snake venom proteins relative to linear RGD peptides is likely due to a specific conformation of the RGD epitope while the rest of the protein may simply provide the rigidity and the stability to present this epitope to the receptor.

Decorsin and ornatin are similar in both size and cysteine content to a number of serine protease inhibitor proteins that have been isolated from leeches. These include hirudin and isoforms of hirudin, which are potent thrombin inhibitors, and the bdellins, which are inhibitors of trypsin and plasmin (Seemuller, U., Dodt, J., Fink, E., and Fritz, H. (1986) in *Proteinase Inhibitors*, Barrett, A. J. and Salveson, G., eds., (Elsevier, Amsterdam) Ch. 8, pp. 337-339). However, there is no apparent primary sequence homology between decorsin or ornatin and these proteins. The high proline and cysteine content, assuming that all of the cysteines are present in disulfide bonds (consistent with the FAB-MS data) suggests that decorsin and ornatin have very rigid structures. A search of the Dayhoff protein sequence database failed to identify any proteins with substantial homology to either decorsin or ornatin.

The function of decorsin in *M. decora* and ornatin in *P. ornata* are not known, although it is possible that these proteins serve to keep the host blood flowing, or to keep ingested blood from coagulating. This second putative function is important because leeches store ingested blood for long periods of time, digesting it slowly as needed (Lent, C. (1986) *Nature* 323, 494).

Recently, potent protein antagonists of GP II$_b$ III$_a$ have been purified and characterized from a large number of snake venoms (see the Description of Background and Relevant Materials for relevant citations). These proteins are quite homologous to one another, and represent a protein family. In some cases, isoforms of these proteins have been observed. Isoforms of proteins from leeches are also well-known: antistasin, from *Haementaria officinalis*; the Factor Xa inhibitor from *Haementaria ghilianii*; and hirudin, from *Hirudo medicinalis*, all have isoforms that possess activity substantially identical to that of their respective native proteins. Presumably, this is due to slight variations in the genes coding for these proteins, which may be undergoing changes attributable to evolutionary pressures.

Accordingly, it is contemplated that there exists a general homologous family of decorsin-like and ornatin-like proteins, for example, decorsin isoforms and decorsin analogs or ornatin isoforms and ornatin analogs, in different hematophagous leech species. These proteins would be substantially identical to decorsin or ornatin, except that they may be expected to possess slight variability in their amino acid sequences that do not significantly affect the activity of the protein (e.g., amino acid changes, deletions, or insertions). For example, it is likely that the RGD sequence is conserved in the decorsin and ornatin protein family, as well as the cysteines, since they are involved in disulfide bonds and hence are probably important to the native structure of the protein family. The prolines may also be conserved. These isoforms or analogs are likely encoded by DNA that is a natural allele of the decorsin or ornatin DNA.

A recent report has indicated that prolonged bleeding occurs after a leech bite for *Hirudo medicinalis* in the apparent absence of hirudin (Munro, R., Hechtel, F.O.P., and Sawyer, R. T. (1989) *Thrombosis and Haemostasis* 61, 366-369). This may be explained in view of the present study, wherein inhibition of Fg binding to GP II$_b$ III$_a$ has been observed in several different leech genera. Based on the findings herein, it is possible that these activities are related to decorsin, decorsin isoforms, decorsin analogs, ornatin, ornatin isoforms, or ornatin analogs that act as GP II$_b$ III$_a$ antagonists.

Production of Decorsin or Ornatin and Isoforms Thereof

By means of the techniques described herein decorsin and ornatin and various isoforms thereof have been identified, purified, and characterized. The characterization of decorsin and ornatin provided herein includes their amino acid sequences and compositions. Based upon this information, decorsin and ornatin can now be obtained in a number of ways.

It is to be understood that, while for purposes of simplicity the present discussion refers only to "decorsin" and "ornatin" the techniques described herein may be used to identify, purify, and characterize isoforms and analogs of decorsin and ornatin, as well as to synthesize, purify, and characterize homologs of these proteins.

Isoforms of decorsin and ornatin refer to naturally-occurring variations of the native decorsin and ornatin amino acid sequence as described herein, which exist within and species possessing native decorsin and ornatin, and which exhibit activity substantially similar to that of native decorsin and ornatin. (For purposes of this discussion, native decorsin refers to decorsin having the 39-amino acid sequence shown for decorsin in Table I.) Leeches may contain not only native decorsin and ornatin, but proteins which differ from native decorsin and ornatin by only a few amino acids and which possess substantially similar activity as GP $II_b III_a$ antagonists or platelet aggregation inhibitors.

For example, the N-2 and N-3 forms of decorsin found in leeches of the species *Macrobdella decora* described herein are isoforms. Isoforms should have at least about 80% homology to the decorsin amino acid sequence.

Analogs of decorsin or ornatin refer to proteins found in other species and other genera other than *Macrobdella decora* and *Placebdella ornata*, but which are evolutionarily related to decorsin and ornatin in that they possess a substantially similar primary structure and exhibit substantially similar activity as GP $II_b III_a$ antagonists or platelet aggregation inhibitors. It is reasonable to expect that numerous other species and genera of leeches possess proteins which, while not identical to decorsin or ornatin, serve the same function and have much the same structure. It should be possible to identify, purify, characterize, and produce such analogs using the techniques of the present invention. Analogs preferable have at least about 70% homology to the decorsin or ornatin amino acid sequences. More preferably analogs have cysteine residues and the RGD sequence in the same number and register as decorsin and ornatin. Most preferably analogs will contain the sequence CXXXRGDXXXXC (Seq. ID No. 11) where X is any amino acid residue.

Homologs of decorsin or ornatin refer to synthetically obtained proteins, not known to exist in nature, which possess a primary structure substantially similar to decorsin or ornatin and which exhibit substantially similar activity as GP $II_b III_a$ antagonists or platelet aggregation inhibitors. Homologs may be synthetically obtained directly via chemical synthesis, or indirectly via construction of nucleic acid sequences encoding the homolog amino acid sequences followed by use of recombinant DNA techniques to obtain large-scale production of the homologs in culture. Chemically synthesized homologs may contain either L or D α-amino acids, which may be either natural or non-natural amino acids. Homologs preferably have at least about 70% homology to the decorsin or ornatin amino acid sequence, and most preferably contain the sequence CXXXRGDXXXXC (Seq. ID No. 11) where X is any amino acid residue.

In defining homology, the protein resulting from the substitution of an amino acid in the decorsin or ornatin amino acid sequence by a conservative analog is considered to be a homologous protein. The recognized categories of conservative amino acid analogs are aromatic residues (F, H, Y, W); charged basic residues (H, K, R); charged acidic residues (D, E); aliphatic neutral nonpolar residues (A, G, I, L, P, V); and aliphatic neutral polar residues (C, M, N, Q, S, T). In addition, insertions or deletions of amino acids may occur within homologous proteins.

The term amino acid, as used herein, refers to naturally-occurring L α-amino acids, unless otherwise specifically indicated. The commonly used one- and three-letter abbreviations for amino acids are use herein (Lehninger, A. L., *Biochemistry*, 2d ed., pp. 71–92, (1975), Worth Publishers, N.Y.).

It is therefore to be understood that while the following discussion may generally be phrased in terms of the production of decorsin or ornatin, it is to be considered as also encompassing production of decorsin and ornatin analogs, homologs, and isoforms.

One method of production involves chemical synthesis of the protein (see Barany and Merrifield, ibid.), followed by treatment under oxidizing conditions appropriate to obtain the native conformation, that is, the correct disulfide bond linkages. This can be accomplished using methodologies well known to those skilled in the art (see Kelley, R. F. and Winkler, M. E., (1990) in *Genetic Engineering Principles and Methods*, Setlow, J. K., ed., Plenum Press, N.Y., vol. 12, 1–19).

An alternative approach contemplates the use of recombinant DNA technology to produce large quantities of decorsin or ornatin. Analogs, isoforms, or homologs of decorsin or ornatin may also be produced using site directed mutagenesis (Carter, P., et al., (1986) *Nucl. Acids Res.* 13, 4331; Zoller, M. J., et al. (1982) *Nucl. Acids Res.* 10, 6487), cassette mutagenesis (Wells, J. A., et al. (1986) *Philos. Trans. R. Soc. London* SerA 317,415) or other known techniques. The result of the employment of such techniques is the production of mutant DNA, which encodes for changes in amino acid sequence of the resultant protein relative to the parent decorsin or ornatin molecule.

While the following discussion generally relates to methodologies of protein production utilizing particular recombinant DNA techniques, it is to be understood that the disclosure of the present application should permit those of ordinary skill in the art to produce decorsin or ornatin and their isoforms, analogs, or homologs by any conventional technique.

"Expression vector" refers to a DNA construct containing a DNA sequence which is operably linked to a suitable control sequence capable of effecting the expression of said DNA in a suitable host. Such control sequences generally include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert.

Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or which become, known in the art.

"Operably linked," when describing the relationship between two DNA or polypeptide regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

Gene Synthesis, Cloning, and Expression.

General Procedures

From the purified protein and its amino acid sequence, decorsin or ornatin may be produced using recombinant DNA techniques. These techniques contemplate, in simplified form, taking the gene for either decorsin or ornatin; inserting it into an appropriate vector; inserting the vector into an appropriate host cell; culturing the host cell to cause expression of the decorsin or ornatin gene; and purifying the protein produced thereby.

Somewhat more particularly, the DNA sequence encoding either decorsin or ornatin is cloned and manipulated so that it may be expressed in a convenient host. DNA encoding parent polypeptides can be obtained from a genomic library, from cDNA derived from mRNA from cells expressing decorsin or ornatin and their isoforms, or by synthetically constructing the DNA sequence (Sambrook, J., Fritsch, E. F., and Maniatis, T., (1989), *Molecular Cloning* (2d ed.), Cold Springs Harbor Laboratory, New York).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, *E. coli* may be transformed using pBR322, a plasmid derived from an *E. coli* species (Mandel, M. et al. (1970) *J. Mol. Biol*, 53, 154). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A preferred vector is pB0475. This vector contains origins of replication for phage and *E. coli* which allow it to be shuttled between such hosts, thereby facilitating both mutagenesis and expression (Cunningham, B., et al. (1989), *Science* 243, 1330-1336; Wells, J. and Cunningham, B., co-pending application U.S. Ser. No. 07/428,066 filed Oct. 26, 1989. Other preferred vectors are pR1T5 and pR1T2T (Pharmacia Biotechnology). These vectors contain appropriate promoters followed by the Z domain of protein A, allowing genes inserted into the vectors to be expressed as fusion proteins. Further discussion of these vectors may be found below.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce parent polypeptides, segment substituted polypeptides, residue-substituted polypeptides and polypeptides variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various pseudomonas species. The preferred prokaryote is *E. coli* W3110 (ATCC 27325). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture*, Academic Press, Kruse and Patterson, editors (1973)). Examples of such useful host cell lines are VERO and HeLa cells, Chinese Hamster Ovary (CHO) cell lines, W138, 293, BHK, COS-7 and MDCK cell lines.

Gene Fusions

A variation on the above procedures contemplates the use of gene fusions, wherein the gene encoding the desired protein is associated, in the vector, with a gene encoding another protein or a gragment of another protein. This results in the desired protein-here, decorsin or ornatin-being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. (1983) in *Genetic Engineering*, Willamson, R., Ed., Academic, London, Vol. 4, p. 127; Uhlen, M., Moks, To. (1989) *Methods Enzymol*, (in press)). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli*, but are stable when expressed as fusion proteins (Marston, F. A. O., (1986) *Biochem J.* 240, 1).

Decorsin or ornatin expressed as fusion proteins may be properly folded or require folding to obtain the native structure. The properly folded fusion protein may be active and useful as a GP II$_b$ III$_a$ antagonist and inhibitor of platelet aggregation. More preferred would be the correctly folded native protein that is obtained from the fusion protein by methods known in the art. Fusion proteins can be cleaved using chemicals, such as cyanogen bromide, which cleaves at a methionine, or hydroxylamine, which cleaves between an asn and gly. Using standard recombinant DNA methodology, the nucleotide base pairs encoding these amino acids may be inserted just prior to the 5' end of the decorsin or ornatin gene.

Alternatively, one can employ proteolytic cleavage of fusion proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants, and a number of other have been successfully used to cleave fusion proteins. Typically, a peptide linker that is amenable to cleavage by the protease used is inserted between the "other" protein (e.g., the Z domain of protein A) and the protein of interest, such as decorsin or ornatin. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The protein may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the protein is treated with a chaotrope, such a guanidine HCl, and is then treated with a redox buffer, containing, for example, reduced and oxidized dithiothreitol or glutathione at the appropriate ratios, pH, and temperature, such that the protein of interest is refolded to its native structure.

The following procedures describe two constructions for protein A/decorsin fusion protein expression, followed by a procedure for a construction which allows for direct (i.e., non-fusion protein), secreted expression of decorsin. These procedures involve the design of two synthetic "cassettes," which is also explained below; the first cassette is designed for the expression of fusion proteins, and the second cassette is designed for the direct expression of decorsin. These procedures are intended to be illustrative only, and are not to be considered as in any way limiting on the scope of the present invention. It will be understood by one of ordinary skill in the art that these illustrative procedures could easily be adopted to produce ornatin from its amino acid sequence or any other protein encompassed by this disclosure.

Synthesis of the Decorsin Gene

Based on the foregoing amino acid composition and sequence analysis, a gene for decorsin can be assembled from 6 synthetic DNA oligonucleotides using standard methodologies. (Sambrook, J. et al. (1989) *Molecular Cloning, a Laboratory Manual*, second edition, CSH). The oligonucleotide sequences encode the amino acid sequence of decorsin and are designed such that unique restriction sites are conveniently located for use in site specific mutagenesis procedures. Additionally, the oligonucleotide sequences of the fusion cassette are designed so that, once assembled, the synthetic gene will have an EcoRI 5' overhang at the beginning of the sequence and a PstI 3' overhang at the beginning of the sequence, with additional restriction sites inserted downstream of the decorsin coding sequence; these enable the gene to be shuttled between different vectors (FIG. 6).

The oligonucleotides range from 34 to 70 base pairs long, and share a unique 4 base pair overlap with neighboring oligonucleotides. The synthetic oligonucleotide sequence of the fusion cassette includes a 22 base pair linker upstream of the decorsin gene which encodes a cleavage site amenable to cleavage by thrombin (Reinach, F. C., et al., (1986) *Nature*, 322, 80–83) and factor Xa (Nagai, K. et al., *Methods in Enzymology*, 153, 461–481); this cleavage side is used to generate decorsin from the fusion protein.

In the three constructions described below, the first allows the fusion protein to be secreted into the periplasmic space of *E. coli*; the second construction provides for intracellular expression of the fusion protein; and the third construction provides for direct, secreted expression of decorsin.

Construction Synthetic Gene for Protein A/Decorsin Fusion Protein

The synthetic DNA oligonucleotides which will be assembled to form the decorsin gene are synthesized using standard methodologies (Crea, R., and Horn, T., (1980) *Nucl. Acids Res.*, 8, 2231). In order to form the synthetic gene with its attached linker for the fusion protein constructions, the individual DNA nucleotides are phosphorylated and annealed together in pairs by gradual cooling from 85° C. to 20° C.

The double stranded DNA segments are then ligated together with protein A gene fusion vector pRIT5 (PharmaciaLKB Biotechnology) previously digested with EcoRI and PstI. This vector contains a broad host range origin of replication, the chloramphenicol acetyltransferase gene from pC194 (Horinouchi, S. and Weisblum, B. (1982) *J. Bacteriol*, 150, 815), and the origin and ampicillin resistance gene from pBR322. pRIT5 also contains the protein A promoter and encodes the protein A signal sequence followed by the Z domain (synthetic IgG binding domain) or protein A, which leads directly into a multiple cloning site. Thus, genes inserted into the multiple cloning site are expressed from the protein A promoter as secreted Z domain fusion. This construction is referred to as pZdecorsinS.

Periplasmic Secretion of the Fusion Protein

When *E. coli* or other host cells are transformed with pZdecorsinS and the fusion protein is expressed, the presence of the protein A signal sequence causes the fusion protein to be secreted into the periplasmic space. An example of a procedure to obtain the protein fusion follows:

pZdecorsinS is transformed into *E. coli* strain JM101 and plated on LB agar containing 50 µg/ml carbenicillin. DNA from several of the carbenicillin resistant colonies is isolated using standard miniprep procedures (Sambrook, J., et al., ibid.), and is then subjected to restriction analysis. The DNA of the clones which appears to contain the correct insert size is then cut with EcoRI and PstI and the resulting insert fragment encoding the cleavage site linker and the decorsin gene is isolated and inserted into the multiple cloning site of M13 for sequencing according to standard protocols (Sanger, F., Nicklen, S., and A. R. Coulsen, (1977) *Proc. Natl. Acad. Sci. USA*, 74, 5463–5467).

Clones containing the correct DNA sequence encoding the protein A/decorsin fusion protein (i.e., *E. coli*

JM101, *E. coli* W3110, or *E. coli* K12 strain 294, transformed with the pZdecorsinS plasmid) are inoculated into LB broth containing 50 μg/ml carbenicillin and grown for 16 hours at 37° C. on a rotary shaker (O.D.$_{550}$=2 to 2.5). The cells are harvested by centrifugation and frozen at −20° C. for 1 hour, then subjected to osmotic shock by resuspension in 10 mM Tris, pH 7.5 and incubation at 4° C. for 1 hour. The suspension is centrifuged and the supernatant is transferred to a tube containing IgG Sepharose equilibrated in 50 mM Tris-HCl, pH 7.5, 150 mM NaCl, and 0.05% Tween 20. The mixture is shaken at room temperature for 20 minutes, the IgG Sepharose is allowed to settle to the bottom, and the supernatant is discarded.

The IgG Sepharose, now having Z-decorsin bound to it, is washed with equilibration buffer followed by 0.5 mM ammonium acetate, pH 6.5, and then transferred to a column. The Z-decorsin fusion is eluted with 1M acetic acid, and lyophilized. The dried Z-decorsin fusion is then solubilized in 40 mM Tris, pH 8.0, 100 mM NaCl, and digested with, for example, either Factor Xa or thrombin using standard digestion conditions (Carter, P., ibid.), at a ratio of about 1:250 enzyme/protein (w/w) for about 2.5 hours, or longer, at 20° C. Cleaved decorsin is then purified by reversed phase HPLC as described herein. The decorsin fusion can also be reduced by dithiothreitol, cleaved, and then refolded using the methods described herein.

Intracellular Expression of the Fusion Protein

To obtain intracellular expression of the protein A/decorsin fusion protein, the second construction involves isolating the linker-decorsin fragment from pZdecorsinS by cutting with EcoRI and PstI, and ligating that fragment into pRIT2T (PharmaciaLKB Biotechnology) that has been cut with EcoRI and PstI. pRIT2T contains the lambda P$_R$ promoter, followed by a portion of the lambda cro gene fused to the Z domain of protein A, and a multiple cloning site.

Insertion of the EcoRI-PstI fragment encoding the linker and the decorsin gene from pZdecorsinS into this multiple cloning site allows expression of the protein A/decorsin fusion protein from the lambda P$_R$ promoter. Since this vector lacks a signal sequence, the fusion protein is expressed intracellularly. *E. coli* or other suitable hosts are transformed with pZdecorsinI as previously described. This construction, referred to as pZdecorsinI, is grown in an *E. coli* host which carries the temperature-sensitive repressor C1857 (*E. coli* N4830-1), allowing thermo-inducible expression of the fusion protein. The DNA from several ampicillin resistant colonies is isolated and subjected to restriction analysis followed by subcloning and DNA sequencing.

Clones containing the correct DNA sequence encoding the protein A/decorsin fusion protein (i.e., *E. coli* N4830-1 transformed with the pZdecorsinI plasmid) are inoculated into LB and grown at 30° C. to an optical density of 1.0 measured at 550 nm. The culture is then diluted with an equal volume of fresh LB warmed to 65° C., and grown at 42° C. for 1.5 hours to induce expression.

The cells are harvested by centrifugation and frozen at −20° C. overnight. The thawed pellets are resuspended in 20 mM Tris, pH 7.5, 1 mM EDTA, and 0.05% Tween 20 containing 2 mg/ml hen egg white lysozyme. The suspension is stirred for 1 hour at 4° C., and then MgSO$_4$ and DNAase are added to final concentrations of 5 mM and 1 μg/ml, respectively. Sonication can also be used to obtain the cytoplasmic material.

After an additional 30 minutes of stirring, the cell debris is removed by centrifugation. The supernatant is then transferred to a tube containing IgG sepharose, and the protein A/decorsin fusion protein is purified and cleaved as described above.

Depending on growth conditions, cells expressing high levels of heterologous proteins sometimes form refractile bodies, which contain the insoluble protein. In this case, the refractile bodies are first isolated by know methods (Kelley, R. F. and Winkler, M. E., ibid.; Nagai, K. et al. *Method in Enzymology*, 153, 461–481). After decreasing the denaturant concentration by dilution or dialysis, decorsin is purified as described above. Again the decorsin protein can be isolated by a combination of reduction, cleavage, and refolding to yield the native protein.

Direct Expression of Decorsin

The oligonucleotides utilized for the direct expression of decorsin are similar to those used for expression of the fusion protein, except that the linker region is omitted, and the oligonucleotide sequences that begin and end the gene are designed so that, once assembled, the synthetic gene will have an PstI 3' overhang at the beginning of the sequence and a BglII 5' overhang at the end of the sequence (FIG. 7).

In order to construct the synthetic gene for direct expression or decorsin, the individual oligonucleotides are phosphorylated and then annealed together in pairs by gradual cooling from 85° C. to 20° C. The double stranded DNA segments are then ligated together with the 4.7 kb fragment of pBO475 which has been isolated after restriction with NsiI and BglII. This construction is referred to as pDecorsin.

pBO475 contains the alkaline phosphatase promoter, followed by the stII signal and the gene encoding human growth hormone on an NsiI-Bgl II fragment, as well as the bacteriophage F1 and pMB1 origins of replication and the ampicillin resistance gene (Cunningham, B. C. et al. (1989) *Science* 243, 1330–1336; Wells J. and Cunningham, B., co-pending application U.S. Ser. No. 07/428,066, filed Oct. 26, 1989). pDecorsin is transformed into *E. coli* strain JM101 (or another suitable *E. coli* strain) and plated on LB agar containing 50 μg/ml carbenicillin. DNA from several of the carbenicillin resistant colonies is isolated using standard miniprep procedures (Sambrook, J. et al., ibid.), and is then subjected to restriction analysis. The DNA of the clones which appears to contain the correct insert size is then sequenced according to standard protocols (Sanger, F., Nicklen, S., and A. R. Coulsen, (1977) *Proc. Natl. Acad. Sci. USA* 74, 5463–5467). Clones containing the correct DNA sequence encoding the decorsin sequence are inoculated into LB containing 50 μg/ml carbenicillin, and grown for 16 hours at 37° C. on a rotary shaker (O.D.$_{550}$—2.0 to 2.5). The cells are harvested by centrifugation and frozen at −20° C. for 1 hour, then subjected to osmotic shock by resuspension in 10 mM Tris-HCl, pH 7.5 and incubation at 4° C. for 1 hour. The suspension is centrifuged and the supernatant is filtered through a 30,000 molecular weight cutoff membrane (YM30, Amicon Corp., Lexington, Mass.) to remove high molecular weight contaminants. The YM30 flow through is then loaded onto a preparative C18 resin (Nugel P-RP, Separation Industries, Metuchen, N.J.) equilibrated in water containing 0.1% TFA. After loading and washing the column with equilibration buffer, the protein is eluted with 50% acetonitrile, 0.1% TFA. The eluted protein is lyophilized and resolubilized in water and chromatographed on a Vydac C18 reversed phase HPLC column equilibrated in water, 0.1% TFA and eluted with a linear acetonitrile gradient. Alternatively, the GP $II_b III_a$ affinity column (as described herein) can be used to purify the decorsin prior to the final HPLC step.

Mutant DNA Production

As previously discussed, various techniques are also available which may now be employed to produce mutant decorsin or ornatin DNA, which encodes for additions, deletions, or changes in amino acid sequence of the resultant protein relative to the parent decorsin or ornatin molecule (i.e., decorsin analogs, decorsin isoforms, decorsin homologs, ornatin analogs, ornatin isoforms, or ornatin homologs).

Specifically, by way of illustration, with pZdecorsinS, pZdecorsinI, pDecorsin, or pOrnE (see Example L) in hand, site specific mutagenesis (Carter, P., et al., (1986) *Nucl. Acids. Res.* 13, 4331; Zoller, J. J., et al. (1982) *Nucl. Acids Res.* 10, 6487), cassette mutagenesis (Wells, J. A., et al (1985) *Gene* 34, 315), restriction selection mutagenesis (Wells, J. A., et al. (1986) *Philos. Trans, R. Soc. London SerA* 317, 415) or other known techniques may be performed on the decorsin or ornatin DNA. The mutant DNA can then be used in place of the parent DNA by insertion into the aforementioned expression vectors. Growth of host bacteria containing the expression vectors with the mutant DNA allows the production of mutant decorsin or ornatin (i.e., analogs, isoforms, or homologs of decorsin or ornatin), which can be isolated as previously described herein.

Applications

As previously indicated, many common human disorders are characteristically associated with a hypercoagulable state leading to intravascular thrombi and emboli. These are a major cause of medical morbidity, leading to phlebitis, infarction, and stroke, and of mortality, from stroke and pulmonary and cardiac emboli. A large percentage of such patients have no antecedent risk factors, and develop venous thrombophlebitis and subsequent pulmonary emboli without a known cause. Other patients who form venous thrombi have underlying diseases known to predispose to these syndromes.

Some of these patients may have genetic or acquired deficiencies of factors that normally prevent hypercoagulability, such as anti-thrombin 3. Others have mechanical obstructions to venous flow, such as tumor masses, that lead to low flow states and thrombosis. Patients with malignancy have a high incidence of thrombotic phenomena, for unclear reasons. Anti-thrombotic therapy in this situation with currently available agents is dangerous and often ineffective.

Patients with atherosclerosis are predisposed to arterial thromboembolic phenomena for a variety of reasons. Atherosclerotic plaques form niduses for platelet plugs and thrombi that lead to vascular narrowing and occlusion, resulting in myocardial and cerebral ischemic disease. Thrombi that break off and are released into the circulation can cause infarction of different organs, especially the brain, extremities, heart and kidneys. After myocardial infarctions, clots can form in weak, poorly functioning cardiac chambers and be released into the circulation to cause emboli. All such patients with atrial fibrillation are felt to be at great risk for stroke and require antithrombotic therapy.

In addition, thrombolytic therapy for acute myocardial infarction has become an established procedure for patients (Collen, D. and Stump, D. (1988) *Ann Rev Med* 39, 405–423). However, currently available thrombolytic agents are not effective in all patients which is manifest by reocclusion, resistance to reperfusion, prolonged times to achieve normal coronary flow and the like. Since platelet mediated thrombosis is a major mechanism involved in the efficacy of thrombolytic therapy, agents which can be used to affect platelet aggregation in adjunctive therapy to treat acute myocardial infarction would have significant beneficial effects. Suitable thrombolytic agents include: tissue plasminogen activator, streptokinase, urokinase, prourokinase, and modifications thereof.

Patients whose blood flows over artificial surfaces, such as prosthetic synthetic cardiac valves or through extracorporeal perfusion devices, are also at risk for the development of platelet plugs, thrombi, and emboli. It is standard practice that patients with artificial cardiac valves be chronically anti-coagulated.

Thus, a large category of patients, including those with cancer, atherosclerosis, coronary artery disease, artificial heart valves, and a history of stroke, phlebitis, or pulmonary emboli, are candidates for limited or chronic antithrombotic therapy. However, this therapy is often ineffective or morbid in its own right. This is partially because the number of available therapeutic agents is limited and these, for the most part, act by reducing levels of circulating clotting factors. These agents are, therefore, not necessarily aimed at the patient's underlying hematologic problem, which often concerns an increased propensity for platelet aggregation and adhesion. They also cause the patient to be very susceptible to abnormal bleeding. Available antiplatelet agents, such as aspirin, inhibit the cyclooxygenase-induced activation of platelets only and are often inadequate for therapy.

Platelet aggregation plays a fundamental role in hemostasis. Although multiple factors, including a variety of physiologic stimuli and soluble mediators, can initiate platelet activation via several pathways, these share the common final step of activation of the GP $II_b III_a$ receptor and its subsequent binding to fibrinogen. This interaction appears to be a final common step of all aggregation pathways.

An agent which effectively inhibits the binding of fibrinogen to its receptor on platelets should accordingly be particularly useful in therapeutic intervention in a large group of disorders characterized by a hypercoagulable state. As the binding of integrin receptors with their ligand characterizes the adherence of cells to basement membrane proteins and is felt to be a necessary and important step in the invasion and metastasis of tumor cells, such inhibitors are also of interest as potential antineoplastic agents. Ideally, such an agent would additionally demonstrate little or no antigenicity, thereby avoiding interference with the agent's activity resulting from its recognition and targeting by the host immune system.

Although the antigenicity in humans of the inhibitors described herein is not yet known, other proteins from leeches that affect hemostasis, such as hirudin, are relatively non-antigenic (Markwardt, F., in *Hemostasis and Animal Venoms*, H. Pirkle and F. G. Markland, Jr., eds., Marcel Dekker, N.Y., pp. 255–269 (1988)). Since leeches often return to the same host for feeding, they may have adapted in ways so as to reduce the immunogenicity of their molecules that come into contact with the host. The hypothesis that the inhibitors described herein may also have a relatively low level of antigenicity in humans would, if proved true, have substantial clinical value in the treatment of patients with thrombotic disease.

Because decorsin and ornatin (and their isoforms, analogs, and homologs) inhibit binding between the GP $II_b III_a$ receptor and fibrinogen, it may be expected to antagonize platelet activation by any stimulus. Decorsin or ornatin should therefore have therapeutic effect in any disorder characterized by a hypercoagulable state. Such disorders include, for example, cancer, atherosclerosis, coronary artery disease, artificial heart valves, and a history of stroke, phlebitis, or pulmonary emboli. The formulation of suitable pharmaceutical compositions, choice of application modes (intravenous injection, oral administration, use of sustained release compositions, and the like), and determination of appropriate dosages, may be left to the skilled practitioner.

As a general matter, however, in the management of thromboembolic disorders, the compounds of the present invention may be utilized in compositions such as tablets, capsules, or elixirs for oral administration, suppositories for rectal administration, and the like. Animals in need of treatment using compounds of the present invention can be administered dosages that will provide optimal efficacy. The dose and method of administration will vary from animal to animal, and be dependent upon such factors as weight, diet, concurrent medication, and other factors which those skilled in the medical arts will recognize.

Dosage formulations of the compounds of the present invention are prepared for storage or administration by mixing the compound having the desired degree of purity with physiologically acceptable carriers, excipients, or stabilizers. Such materials are nontoxic to the recipients at the dosages and concentrations employed, and include buffers such as phosphate, citrate, acetate, and other organic acid salts; antioxidants such as ascorbic acid; low molecular weight (i.e., less than about 10 residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as Tween, Pluronics, or polyethyleneglycol.

Dosage formulations of the compounds of the present invention to be used for therapeutic applications must be sterile. Sterility is readily accomplished by filtration through sterile filtration membranes such as $0.2\mu$ membranes. Protein formulations ordinarily will be stored in lyophilized form or as an aqueous solution. The pH of the protein preparations typically will be between about 3 and 11, more preferably from about 5 to 9, and most preferably from about 7 to 8. While the preferred route of administration is by hypodermic needle, other methods of administration are also anticipated, such as suppositories, aerosols, oral dosage formulations, sustained release compositions, and topical formulations such as ointments, drops, and dermal patches.

Therapeutic protein formulations are generally placed into a container having a sterile access port, for example, an intravenous solution bag or vial having a stopper pierceable by a hypodermic injection needle.

Therapeutically effective dosages may be determined by either in vitro or in vivo methods. Two methods of evaluating therapeutically effective dosages are to measure a 50% inhibitory concentration ($IC_{50}$), using the GP $II_b III_a$/Fg ELISA or the platelet aggregation assay, both as described herein. Based upon such in vitro assay techniques, a therapeutically effective dosage range may be determined. The range of therapeutically effective dosages will naturally be affected by the route of administration. For injection by hypodermic needle, it may be assumed that the dosage is delivered into the body's fluids. For other routes of administration, the adsorption efficiency must be individually determined for decorsin or ornatin by methods well-known in pharmacology.

The range of therapeutic dosages may range from about 0.001 nM to about 1.0 mM, more preferably from about 0.1 nM to about 100 $\mu$M, and most preferably from about 1.0 nM to about 50 $\mu$M.

A typical formulation of decorsin or ornatin as a pharmaceutical composition contains from about 0.5 to 500 mg of a compound or mixture of compounds as either the free acid or base form or as a pharmaceutically acceptable salt. These compounds or mixtures are then compounded with a physiologically acceptable vehicle, carrier, excipient, binder, preservative, stabilizer, or flavor, etc., as called for by accepted pharmaceutical practice. The amount of active ingredient in these compositions is such that a suitable dosage in the range indicated is obtained.

Typical adjuvants which may be incorporated into tablets, capsules, and the like are a binder such as acacia, corn starch, or gelatin; an excipient such as microcrystalline cellulose; and disintegrating agent like corn starch or alginic acid; a lubricant such as magnesium stearate; a sweetening agent such as sucrose, lactose, or aspartame; and a flavoring agent such as peppermint, wintergreen, orange, grape, or cherry. When the dosage form is a capsule, in addition to the above materials it may also contain a liquid carrier such as fatty oil. Other materials of various types may be used as coating or as modifiers of the physical form of the dosage unit. A syrup or elixir may contain the active compound, a sweetener such as sucrose, preservatives such as proply paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

EXAMPLES

Throughout the following examples, materials employed were obtained or produced from commercial suppliers or by standard procedures and as specifically described below.

Live *Placobdella ornata* were obtained from Cyr's Biology Company (Ponchatoula, La.: live *Macrobdella decora* were purchased from St. Croix Biological Supply (Stillwater, Minn.). The leeches were maintained in nonchlorinated mineral water at room temperature prior to use. GP $II_b III_a$ was purified from outdated human platelets as previously described and was stored at $-80°$ C. in TACTS buffer prior to use (Dennis, M. S., Henzel, W. J., Pitti, R. M., Lipari, M. T., Napier, M. A., Deisher, T. A., Bunting, S. and Lazarus, R. A. (1990) *Proc. Natl. Acad. Sci.* USA, 87, 2471-2475; and Seymour, J. L., Henzel, W. J., Nevins, B., Stults, J. T., and Lazarus, R. A. (1990) *J. Biol. Chem.* 265, 10143-10147). Human fibrinogen from Kabi (Uppsala, Sweden) was further purified as previously described (Dennis, M. S., Henzel, W. J., Pitti, R. M., Lipari, M. T., Napier, M.A., Deisher, T. A., Bunting, S. and Lazarus, R. A. (1990) *Proc. Natl. Acad. Sci.* USA, 87, 2471-2475; and Seymour, J. L., Henzel, W. J., Nevins, B., Stults, J. T., and Lazarus, R. A. (1990) *J. Biol. Chem.* 265, 10143-10147). AP3, a murine monoclonal to human GP $II_b III_a$ (Newman, P. J., Allen, R. W., Kahn, R. A., and Kunicki, T. J. (1985) *Blood* 65, 227-232) was provided by Dr. P. Newman (Blood Center at Southeastern Wisconsin, Milwaukee). Goat anti-mouse IgG conjugated to horseradish peroxidase was purchased from Tago (Burlingame, Calif.). O-phenylenediamine dihydrochloride was from Sigma (St. Louis, Mo.) Tween 20, molecular weight standards, and Affiprep 10 resin were purchased from BioRad (Richmond, Calif.). Sephadex G-50 and electrophoresis supplies and equipment were purchased from PharmaciaLKB (Piscataway, N.J.). Endoproteinase asp-N was purchased from Boehringer Mannheim (Indianapolis, Ind.). Trifluoroacetic acid (TFA) and trichloroacetic acid (TCA) were purchased from Pierce (Rockford, Ill.). The peptide GRGDV was synthesized by solid phase methodology and characterized as previously described (Dennis, M. S., Henzel, W. J., Pitti, R. M., Lipari, M. T., Napier, M. A., Deisher, T. A., Bunting, S. and Lazarus, R. A. (1990) *Proc. Natl. Acad. Sci.* USA, 87, 2471-2475; and Seymour, J. L., Henzel, W. J., Nevins, B., Stults, J. T., and Lazarus, R. A. (1990) *J. Biol. Chem.* 265, 10143-10147).

The following methods were employed throughout the Examples. Other art standard methods were employed unless otherwise specified.

Protein Concentration

Protein concentration was determined by the method of Bradford (Bradford, M. M. (1976) *Anal. Biochem.* 72, 248-254) using bovine serum albumin as standard, or by amino acid analysis, as described below.

Electrophoresis

SDS polyacrylamide gel electrophoresis was performed using the Pharmacia PhastGel System. 8% to 25% acrylamide gradient gels were electrophoresed and subsequently silver stained in the staining unit according to Pharmacia protocols. The samples were reduced with 40 mM dithiothreitol and incubated at $100°$ C. for 5 minutes prior to loading the gel.

Fibrinogen/GP $II_b III_a$ ELISA and Platelet Aggregation Assays

The Fg/GP $II_b III_a$ ELISA was performed as previously described (Dennis, M. S., Henzel, W. J., Pitti, R. M., Lipari, M. T., Napier, M. A., Deisher, T. A., Bunting S. and Lazarus, R. A. (1990) *Proc. Natl. Acad. Sci.* USA, 87, 2471-2475; and Seymour, J. L., Henzel, W. J., Nevins, B., Stults, J. T., and Lazarus, R. A. (1990) *J. Biol. Chem.* 265, 10143-10147). Platelet aggregation assays were carried out in human platelet rich plasma (PRP) as reported earlier (Dennis, M. S., Henzel, W. J., Pitti, R. M., Lipari, M. T., Napier, M. A., Deisher, T. A., Bunting, S. and Lazarus, R. A. (1990) *Proc. Natl. Acad. Sci.* USA, 87, 2471-2475; and Seymour, J. L., Henzel, W. J., nevins, B., Stults, J. T., and Lazarus, R. A. (1990) *J. Biol. Chem.* 265, 10143-10147).

EXAMPLE A

Screening of Leech Homogenates

Extracts from several types of leeches (*Macrobdella decora, Placobdella ornata, Hirudo medicinalis*, and *Haemopis grandis*) were screened in the GP $II_b III_a$/Fg ELISA using the following protocol: live leeches were chopped, weighed, and homogenized with TACTS buffer (1 ml buffer per gram of tissue) in a Tissuemizer (Tekmar, Cincinnati, Ohio) tissue homogenizer. The homogenate was centrifuged at 10,000 rpm for 15 minutes in a SS-34 rotor (Sorvall) at $4°$ C. to remove debris. The supernatants were then serially diluted and assayed in the GP $II_b III_a$/Fg ELISA. The data illustrated in FIG. 1 compares the dose dependent response of the ELISA to four such leech extracts at equal protein concentrations. All of the extracts exhibit apparent inhibition of GP $II_b III_a$/Fg binding.

EXAMPLE B

Purification of Decorsin from Crude Leech Homogenate

The protein was purified to apparent homogeneity from a crude extract of whole leech homogenate of *Macrobdella decora* by treatment with trifluoroacetic acid (TFA), followed by GP $II_b III_a$ affinity chromatography, and C18 reverse phase HPLC.

500 g of leeches were homogenized in 400 ml TACTS buffer in a Waring blender. The homogenate was spun at 8,000 rpm for 20 minutes in a GS3 rotor using a Sorvall RC5B refrigerated centrifuge. The supernatant was saved and the pellets were extracted again with 225 ml TACTS buffer in a Tissuemizer (Tekmar, Cincinnati, Ohio) tissue homogenizer. The homogenate was spun as before, and the supernatants from both extractions were pooled to form the crude extract.

The crude extract was stirred magnetically at room temperature while 50% TFA was added dropwise to a final concentration of 1%. Following the addition of TFA, the mixture was stirred at room temperature for 5 minutes and then spun at 12,000 rpm for 20 minutes in GSA rotor. The pellets were discarded and the supernatant was neutralized to pH 7.6 by the dropwise addition of ammonium hydroxide. The neutralized extract was spun at 12,000 rpm for 45 minutes in a GSA rotor; the supernatant was then used directly or stored frozen at $-80°$ C. prior to use.

The neutralized TFA supernatant pool was then loaded onto a $0.5 \times 7$ cm GP $II_b III_a$ affinity column, which was prepared as follows:

Immediately before coupling, approximately 10 ml Affi-Prep 10 resin was washed with 300 ml ice cold 50 mM sodium acetate, pH 4.5 in a coarse sintered glass funnel. After removing excess buffer, approximately 4 ml washed resin was transferred to a 15 ml conical tube containing 8 mg purified GP $II_b III_a$ which had been previously dialyzed into 0.1M sodium bicarbonate, 2 mM $CaCl_2$, pH 8.0.

The coupling was carried out on a rocking platform at room temperature for 2 hours, and then overnight at 4° C. Excess reactive groups on the resin were blocked by incubation with 0.1M ethanolamine, 2 mM $CaCl_2$, pH 9.0 for 1 hour at room temperature. The resin was then transferred to a sintered glass funnel, and washed in an alternating fashion with 20 ml aliquots of 0.1M sodium acetate, pH 4.5, and 0.1M Tris, pH 7.5, each containing 0.5M NaCl and 2 mM $CaCl_2$, to remove any non-covalently bound material. A total of approximately 300 ml of each buffer was used in this cycle washing. Finally, the coupled GP $II_b III_a$ resin was washed with 100 ml 50 mM Tris, pH 7.5 containing 2 mM $CaCl_2$ and stored at 4° C. prior to use.

The affinity column (ca. 4 ml of resin) was equilibrated in 50 mM Tris, pH 7.5 containing 2 mM $CaCl_2$. The neutralized TFA pool was loaded onto the column at a flow rate of 0.5 ml/min and 25 ml fractions were collected. The column was washed with equilibration buffer and then decorsin was eluted with 4 column volumes of 4 mM EDTA, 50 mM Tris, pH 7.5. Immediately following elution, 8 mM $CaCl_2$ was added to the EDTA containing fractions and the column was washed with 10 column volumes of 40 mM $CaCl_2$, 50 mM Tris, pH 7.5. The affinity column was then re-equilibrated in starting buffer. The affinity column was maintained at 4° C. throughout these procedures. Both the column flow-through and the elution fractions were assayed for inhibition of GP $II_b III_a$/Fg binding, using the assay described below. The majority of the activity was found in the flow through, indicating that the capacity of the affinity column was exceeded.

The affinity resin could be regenerated after treatment with $Ca^{2+}$, however, the column was reusable only two or three times, losing binding ability with each use. Presumably, this loss of binding ability is due to disruption of the GP $II_b III_a$ calcium dependent complex (Jennings et al. (1982) *J. Biol. Chem.* 257, 10458–10466), although the presence of a GP $II_b III_a$ binding molecule in the TFA supernatants that is not eluted by EDTA cannot be excluded as a possibility.

Figure 2:
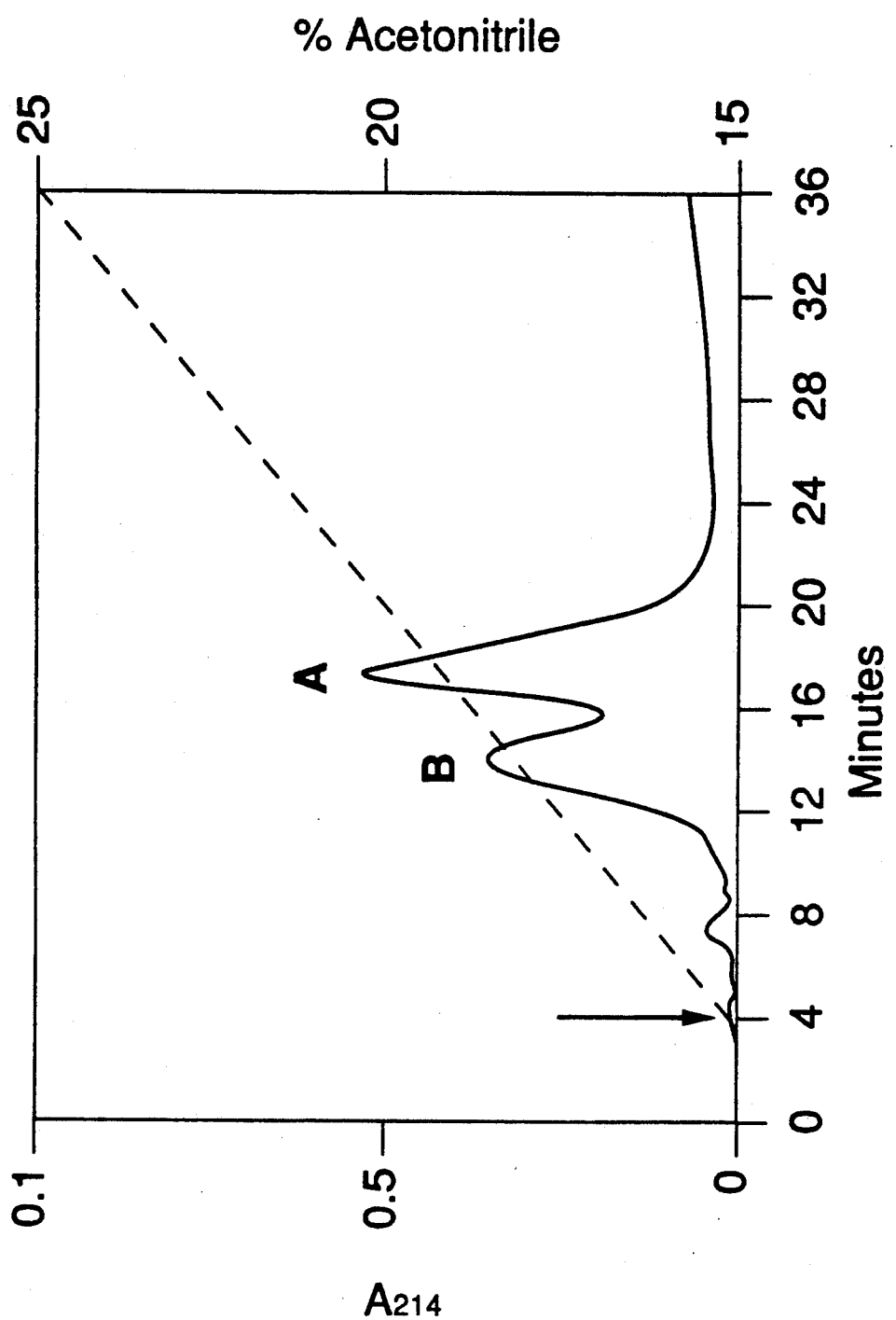

Active fractions from the affinity column were pooled (25–50 ml) and further purified by reverse phase HPLC using a 250 mm×4.6 mm Vydac C18 column (5 μ resin) and Waters model 510 pumps, 680 gradient programmer and 481 uv detector. The column was equilibrated in 90% water/10% acetonitrile, each containing 0.1% TFA, and eluted with a linear gradient of acetonitrile containing 0.1% TFA (0.1% per minute); absorbance was monitored at 214 nm. Fractions containing activity were re-chromatographed and eluted using a gradient of 0.3% per minute (FIG. 2). Prior to activity assays, fractions were vacuum evaporated to dryness, and resolubilized in either $H_2O$ or TACTS buffer. Another activity peak that eluted earlier than decorsin was evident and is discussed below.

The final recovery of decorsin (Peak A, FIG. 2) was ca. 10 μg; this represents less than 10% of the decorsin loaded on the affinity column. Based on a molecular weight of 4378, and assuming a 1:1 stoichiometry, ca. 145 μg represents the theoretical maximum attainable from the 8 mg of GP $II_b III_a$ on the resin, assuming 100% correct orientation of the receptor.

EXAMPLE C

Purification of Decorsin from Leech Ingestate

Decorsin was purified from ingested arginine-saline solution by treatment with trifluoroacetic acid followed by C18 reverse phase HPLC. Leeches were fed a solution of 0.15M NaCl and 2 mM arginine at 42° C. through a Trojan Kling-Tite Naturalamb lambskin condom (Carter Products, New York) and a solution of salivary extract (ingestate) was collected according to the method of Rigbi et al. (1987) *Comp. Biochem. Physiol.* 87B, 567–573).

The solution of salivary extract from 10 leeches was pooled to give 45 ml and stored at −20° C. prior to use. The relative level of contaminating proteins in leech ingestate was far less, based on SDS-PAGE, then in whole leech homogenate, permitting the elimination of the limiting affinity step.

After thawing, the salivary extract was brought to 10% $CH_3CN$ and 0.5% TFA and centrifuged in an SS-34 rotor at 12,000 rpm for 15 minutes. The supernatant was filtered through a 0.45μ filter prior to injection on the C18 reverse phase column; the filtrate had an $A_{280}$ of 0.57. C18 HPLC was then carried out as described above.

Approximately 10 μg of decorsin were isolated from 45 ml of salivary extract. Protein isolated in this manner was identical to decorsin purified from whole leech homogenate based on molecular weight (FAB-MS), amino acid composition, and specific activity ($IC_{50}$) in the GP $II_b III_a$/Fg ELISA.

EXAMPLE D

Decorsin Amino Acid Sequence, Mass spectrommetry, and Composition Analysis

Sequential Edman degradation was performed by loading an aliquot of purified decorsin (ca. 200 pmol) onto a model 470A Applied Biosystems gas phase sequencer equipped with a 120A PTH amino acid analyzer. PTH amino acid peaks were integrated with Nelson Analytical model 3000 data system; data analysis was performed on a Vax 6850 digital Equipment System according to the method of Henzel et al. (Henzel et al. (1987) *J. Chromatogr.* 404, 41–52).

The sequence was consistent with data obtained by fast atom bombardment mass spectroscopy (FAB-MS). An aliquot of the purified protein (ca. 100 pmol) was analyzed as follows:

Protein was vacuum evaporated to dryness and redissolved in 1 μL of 0.1% TFA. This solution was added on the probe tip to 1 μL of glycerol. Mass spectra were obtained with a JEOL HX110HF/HX110HF tandem double-focusing mass spectrometer, using MS-1 only. The instrument was operated at 10 kV accelerating voltage, 500 resolution, and the mass axis was scanned from 100 to 5000 u in 1 minute. The JEOL cesium gun was operated at 2.2 A filament current to produce 15 keV cesium ions. Data were acquired as single scans using the ACM program of the JEOL DA-5000 data system.

The purified protein was found to contain only one major component with a molecular mass of 4379 (based on the observed $M+H^+$ of 4379.9). A doubly charged ion was also observed which confirmed this mass ($M+2H^+ = 2189.9$ which corresponds to $M^+$ of 4377.8). The observed mass is within 1 Da of the mass calculated from the amino acid sequence, assuming that three disulfide bonds are present in the native protein.

Amino acid compositions for decorsin were determined as follows: protein samples were hydrolyzed under vacuum with constant boiling 6N HCl vapor in the Millipore Picotag system for 20 hours at 110° C. The hydrolysates were vacuum evaporated in a Savant speed vac concentrator, and analyzed on a Beckman model 6300 amino acid analyzer equipped with a ninhydrin detector.

As a result of these studies, it was determined that the primary sequence of decorsin is 39 amino acids long (Table I).

TABLE I

Sequence Analysis of Decorsin

| Cycle | Amino Acid | Yield (pmol) |
|---|---|---|
| 1 | Ala | 169 |
| 2 | Pro | 90.5 |
| 3 | Arg | 50.2 |
| 4 | Leu | 82.6 |
| 5 | Pro | 48.2 |
| 6 | Gln | 62.7 |
| 7 | Cys | a |
| 8 | Gln | 48.8 |
| 9 | Gly | 32.8 |
| 10 | Asp | 24.5 |
| 11 | Asp | 38.4 |
| 12 | Gln | 25.1 |
| 13 | Glu | 18.5 |
| 14 | Lys | 17.3 |
| 15 | Cys | a |
| 16 | Leu | 16.5 |
| 17 | Cys | a |
| 18 | Asn | 10.7 |
| 19 | Lys | 14.2 |
| 20 | Asp | 6.8 |
| 21 | Glu | 6.5 |
| 22 | Cys | a |
| 23 | Pro | 7.4 |
| 24 | Pro | 14.1 |
| 25 | Gly | 5.8 |
| 26 | Gln | 5.6 |
| 27 | Cys | a |
| 28 | Arg | 5.9 |
| 29 | Phe | 5.0 |
| 30 | Pro | 3.8 |
| 31 | Arg | 8.3 |
| 32 | Gly | 3.7 |
| 33 | Asp | 2.1 |
| 34 | Ala | 3.2 |
| 35 | Asp | 4.9 |
| 36 | Pro | 2.3 |
| 37 | Tyr | 2.0 |
| 38 | Cys | a |
| 39 | Glu | 0.4 |

[a]Cysteine was identified by the presence of a dehydroalanine peak and absence of a serine peak during this cycle.

The protein contains 6 cysteine and 6 proline residues. The amino acid analysis data matches the composition predicted by amino terminal sequencing, with the exception of the cysteines, which were destroyed during hydrolysis (Table II).

TABLE II

Amino Acid Composition of Decorsin and N-3 Decorsin

| Amino Acid | Decorsin | N-3 Decorsin |
|---|---|---|
| Asp | 6.43 (6)[a] | 6.33 (6) |
| Ser | 0.16 (0) | 0.46 ( ) |
| Glu | 6.31 (7) | 6.23 (7) |
| Gly | 3.07 (3) | 3.21 (3) |
| Ala | 1.71 (2) | 1.09 (1) |
| Cys | 4.09 (6) | 2.54 (6) |
| Ile | 0.04 (0) | 0.08 (0) |
| Leu | 1.96 (2) | 1.95 (2) |
| Tyr | 1.01 (1) | 1.00 (1) |
| Phe | 1.00 (1) | 1.04 (1) |
| Lys | 2.03 (2) | 1.99 (2) |
| Arg | 2.62 (3) | 2.19 (2) |
| Pro | 5.57 (6) | 4.82 (5) |

[a]The numbers in parentheses represent the number of residues determined by amino acid sequence analysis.

Decorsin also contains the sequence Arg-Gly-Asp (RGD), a well-known recognition sequence in many adhesion proteins (Plow, E. F. et al., *Progress in Hemostasis and Thrombosis*, Coller, B. S., ed., (W. B. Saunders Company, Philadelphia), Vol. 9, pp. 117–156), near its C-terminus.

The calculated molecular weight of the reduced protein is 4384; the calculated pI is 4.45.

Evidence for a N-2 and N-3 isoforms, lacking the first two or three amino terminal residues, was also discovered. During the sequencing of purified decorsin, these minor additional sequences were observed. These sequences were identical to decorsin except that they lacked the first two or three amino terminal residues.

The separation of decorsin and the N-3 isoform is shown in FIG. 2. Amino acid composition of Peak B was consistent with N-3 decorsin (Table II).

Thus, decorsin is 39 amino acids long, including 6 cysteine and 6 proline residues; contains the RGD sequence; has a calculated molecular weight of 4384 in its reduced form; and has N-2 and N-3 isoforms which lack the first 2 or 3 N-terminal residues, respectively.

EXAMPLE E

SDS-PAGE Characterization of Decorsin

Decorsin was characterized by SDS polyacrylamide gel electrophoresis using the Pharmacia PhastGel System. 8% to 25% acrylamide gradients gels were electrophorsed and subsequently silver stained in the staining unit according to Pharmacia protocols. The samples were reduced with 40 mM dithiothreitol and incubated at 100° C. for 5 minutes prior to loading the gel.

This analysis revealed a single protein band, at a molecular mass of <14,400 daltons (FIG. 3).

EXAMPLE F

Binding of Decorsin to GP II$_b$ III$_a$

Evidence that decorsin binds to the GP II$_b$ III$_a$ receptor is based on experiments with immobilized GP II$_b$ III$_a$ affinity resin.

After being bound to the resin, decorsin may be eluted from the resin by treatment with EDTA. The EDTA is known to disrupt the calcium dependent heterodimeric structure of GP II$_b$ III$_a$, which is necessary for ligand binding (Jennings, L. K. et al., (1982) *J. Biol. Chem.* 257, 10458–10466). Therefore, the fact that EDTA elutes bound decorsin from GP II$_b$ III$_a$ affinity resin demonstrates that the decorsin was bound to the GP II$_b$ III$_a$ receptor, and that this binding was then disrupted by the action of EDTA.

The interaction of Fg with GP II$_b$ III$_a$, as measured by the ELISA, is also directly inhibited by decorsin. The specific activity (IC$_{50}$) of both decorsin and its N-3 isoform were determined in the ELISA based on the observed dose-dependent response (FIG. 4). The Fg/GP II$_b$ III$_a$ ELISA was performed by a modification of the method of Nachman and Leung (Nachman, R. L. et al. (1982) *J. Clin. Invest.* 69, 263–269) according to the following protocol, with washes of phosphate buffered saline containing 0.01% Tween 20 between each step:

Microtiter plates were coated with purified human fibrinogen (10 μg/ml), washed, and then blocked with TACTS, 0.5% BSA. The plates were washed and samples to be evaluated were added, followed immediately by addition of purified GP II$_b$ III$_a$ (40 μg/ml) in TACTS, 0.5% BSA (Calbiochem). After a 1 hr incubation, the plate was washed and AP3 (1 μg/ml) was added.

Following a 1 hr incubation and another wash, goat anti-mouse IgG conjugated to horseradish peroxidase was added. A final wash was performed, and developing reagent buffer (0.66 mg/ml o-phenylenediamine dihydrochloride, 0.012% H$_2$O$_2$, 22 mM citrate, 50 mM phosphate, pH 5.0) added; plates were incubated until color developed.

The reaction was stopped with 1N H$_2$SO$_4$ and the absorbance at 492 nm measured. A four parameter fit (Marquardt, D. W. (1963) *J. Soc. Indust. Appl. Math* 11, 431–441) was used to estimate the half maximal inhibition concentration.

The results are illustrated in FIG. 4. An IC$_{50}$ of ca. 1.5 nM was calculated for either decorsin or N-3 decorsin. This is considerably more potent that the pentapeptide GRGDV, which has an IC$_{50}$ of ca. 40 nM.

EXAMPLE G

Measurement of Dose-Dependent Inhibition by Decorsin of Platelet Aggregation

Dose-dependent inhibition of human platelet aggregation by decorsin was measured by using decorsin to inhibit ADP-induced platelet aggregation in human platelet rich plasma (PRP). Platelet aggregation assays were performed in PRP as follows:

50 ml whole human blood (9 parts) was drawn on 3.8% Na citrate (1 part) from a donor who had not taken any aspirin or related medication for at least two weeks. Blood was centrifuged at 160×g for 10 minutes at 22° C., allowed to stand for five minutes, and the PRP was decanted. Platelet poor plasma (PPP) was prepared from the remaining blood by centrifugation at 2000×g for 25 minutes at 22° C. PRP platelet count was measured on a Baker 9000 hematology analyzer and diluted to about 300,000 platelets/μL using PPP.

PRP (225 μL) plus 25 μL of either a quantitated solution of decorsin in phosphate-buffered saline (PBS), or PBS alone, was incubated for five minutes in a Chrono-log Aggregometer at 25° C. Light transmittance was recorded after the addition of ADP (8 μM), which initiated platelet aggregation. The inhibition of platelet aggregation was measured at the maximum aggregation response.

Complete inhibition was observed at 1 μM decorsin; an IC$_{50}$ of ca. 300 nM was calculated based on the titration curve. This is much more potent than the pentapeptide GRGDV, which has an IC$_{50}$ of about 75 μM.

Thus, both decorsin and the N-3 isoform inhibit GP II$_b$ III$_a$ binding to immobilized fibrinogen with an IC$_{50}$ of ca. 1.5 nM. Human platelet aggregation induced by ADP is inhibited by decorsin with an IC$_{50}$ of ca. 300 nM; complete inhibition was observed at ≦1 μM.

Based on the GP II$_b$ III$_a$ affinity resin and platelet aggregation assays, decorsin may be expected to function as an exceptionally potent and effective inhibitor of platelet aggregation. Not only does decorsin directly bind to the GP II$_b$ III$_a$ receptor, but it does so with sufficient affinity to yield remarkably high specific activities in both assays.

EXAMPLE H

Chemical Synthesis of Decorsin

Decorsin, and its isoforms, analogs, and homologs, can be prepared by solid phase peptide synthesis (Merrifield, R. (1964) *J. Amer. Chem. Soc.* 85, 2149). The synthesis of decorsin was performed manually on Boc-Glu(OcHx)O-resin (1 gram 0.47 mM., Penisula Labs). The side chains were protected using the following protecting groups: Arg (Tos), Asp (OcHx), Cys (Meb), Glu (OcHx), Lys [X(Cl)], Tyr [Z(Br)], where Tos=tosyl; cHx=cyclohexyl; Meb=4-methylbenzyl; Z(Cl)=2-chlorobenzyloxycarbonyl; and Z(Br)=2-bromobenzyloxy-carbonyl.

Single couplings with BOP (benzotriazol-1-yloxytris(dimethylamino)phosphonium hexafluorophosphate) were performed in DMA (dimethylacetamide). The Boc groups were removed with 55% TFA, 5% ethanedithiol, and 5 % anisole in methylene chloride. Prior to coupling of the next amino acid, the peptide was neutralized with 10% triethylamine in methylene chloride followed by washing with methylene chloride and then DMA. The fully assembled peptide was treated with TFA to remove the BOC group, and then dried prior to removal from the resin. The final peptide-resin weight was 3.58 grams.

Two grams of the protected peptide-resin were suspended in 3.5 ml anisole, 2 ml ethylmethylsulfide, 1 gram p-thiocresol, 0.3 ml triethylsilane in an HF apparatus. The system was purged with nitrogen and the reaction vessel cooled with liquid nitrogen. The reaction vessel was evacuated with high vacuum, and then 35 ml HF was distilled into it. The resin mixture was stirred for 70 minutes at 4° C., the HF was distilled off, and the mixture was dried under high vacuum for 30 minutes. The peptide resin mixture was washed with ether and ethyl acetate. The crude peptide was dissolved in acetic acid, acetonitrile, and water (10/10/80) (V/V/V), and filtered from the resin. The resin was further washed with 10% acetic acid, and the aqueous material combined and lyophilized. This yielded 896 mg of crude reduced decorsin. This material was then purified using HPLC. The peptide was dissolved in 0.1% TFA in water and pumped onto a 2.5×50 cm C$_{18}$ column (15μ, 300 A). A shallow linear gradient of increasing acetonitrile eluted the purified reduced decorsin, as determined by a single peak on analytical HPLC; the molecular weight was confirmed using mass spectrometry.

Reduced decorsin can be lyophilized and stored as a solid. Decorsin can be reduced in the presence of 10 mM dithiothreitol, which can be subsequently dialyzed from the protein.

The reduced decorsin is then refolded to yield the tertiary structure of native decorsin by dissolving the reduced decorsin in dilute TFA (ca. pH 2.0), followed by addition of Tris base to pH 7–8. This is followed by eight stirring at room temperature, or by the addition of reduced and oxidized dithiothreitol or glutathione (1–10 mM total) in a range of ratios from 1:10 to 10:1 of reduced and oxidized forms.

The oxidation is followed by reverse phase HPLC, and the reaction is stopped when oxidation to the native conformation is maximal, usually at about 12 hrs. The native purified decorsin is then isolated from any misfolded forms by purification using reverse phase HPLC. The synthetic native decorsin is essentially identical to that purified from *Macrobdella decora* with respect to its activity in both the GP II$_b$ III$_a$/Fg ELISA, and the platelet aggregation assay.

EXAMPLE I

Purification of Ornatin Isoforms

Activity was monitored throughout the purification using a Fg/GP II$_b$ III$_a$ ELISA. The initial extract was prepared from 310 g of leeches which were minced with a razor blade and extracted six times by homogenizing in 150 ml aliquots of ice cold TACTS buffer, the initial extraction was done in a Waring blender and the rest were carried out in a Tissuemizer (Tekmar, Cincinnati, Ohio) tissue homogenizer. The homogenate was centrifuged (9,500×g for 15 minutes) after each extraction using a Sorvall RC5B refrigerated centrifuge. The supernatants from all extractions were pooled to form the crude extract. The crude extract was stirred magnetically at 4° C. and acidified by dropwise addition of 50% TCA over 30 minutes to a final concentration of 2.5%. The acidified crude extract was stirred an additional 10 minutes and then centrifuged at 9,500×g for 30 minutes. The pellets were discarded and the supernatant neutralized to pH 7.5 by dropwise addition of ammonium hydroxide. The neutralized extract was centrifuged at 9,500×g for 30 minutes, filtered through a 0.22μ disposable filter (Nalgene), and lyophilized to near dryness. The residue was redissolved in 50 mM Tris, pH 7.5, 150 mM NaCl, centrifuged at 27,000×g for 20 minutes, and filtered as above. Half of the neutralized TCA supernatant pool was loaded on a 5×90 cm Sephadex G-50 column at 4° C. equilibrated with 50 mM Tris, pH 7.5, 150 mM NaCl. The column was eluted with the same buffer at a flow rate of 0.65 ml min$^{-1}$; 35 minute fractions were collected. The remaining half was similarly purified, and active fractions from both runs combined to form the G-50 purified pool, which was further purified by GP II$_b$ III$_a$ affinity chromatography. The GP II$_b$ III$_a$ affinity resin was prepared as described previously (Seymour, J. L., Henzel, W. J., Nevins, B., Stults, J. T., and Lazarus, R. A. (1990) *J. Biol. Chem.* 265, 10143–10147), using 75 mg of GP II$_b$ III$_a$ and 50 ml of Affiprep 10 (Biorad). The G-50 purified pool was adjusted to 2 mM CaCl$_2$ and loaded on the 9×2.5 cm affinity column previously equilibrated in 50 mM Tris, pH 7.5, 2 mM CaCl$_2$ at 0.5 ml min$^{-1}$; 25 ml fractions were collected. The column was washed with 750 ml of equilibration buffer at 3 ml min$^{-1}$, and eluted with 500 ml of 10 mM EDTA, 50 mM Tris, pH 8 at ca. 10 ml min$^{-1}$. Immediately following elution, the column was washed with 350 ml of 40 mM CaCl$_2$, 50 mM Tris, pH 7.5, and then re-equilibrated with starting buffer. Active fractions from the loading flow through were pooled, mixed with the affinity resin overnight, and eluted as described above. The eluate from both columns were combined and adjusted to 15 mM CaCl$_2$. All procedures employing the affinity column were carried out at 4° C. The affinity purified pool was concentrated by lyophilization to 47 ml, and the sample filtered as above to remove any precipitate. Final purification was accomplished by reverse phase HPLC on a 250×4.6 mm, 5 μm Vydac C-18 column with Waters model 510 pumps, 680 gradient programmer, and 481 UV detector. The column was equilibrated with 0.1% TFA/water at 1.0 ml min$^{-1}$, and eluted with a linear gradient of 0.1% TFA/acetonitrile which increased at 1.5% min$^{-1}$ for the first 10 minutes, and at 0.1% min$^{-1}$ for the next 100 minutes. Absorbance was monitored at 214 nm; fractions were collected manually. The ornatin A pool was rechromatographed with a 5 to 20% acetonitrile gradient at 0.15% min$^{-1}$. Samples were vacuum evaporated to dryness, redissolved in 500 μl water, and assayed for activity.

EXAMPLE J

Recovery and Properties of Ornatin Isoforms

Several isoforms of ornatin were purified in 4 steps from a crude homogenate extract of the leech *Placobdella ornata*. The isoforms were isolated from a crude extract of whole leeches by acid precipitation with trichloroacetic acid, and further purified by gel filtration chromatography on Sephadex G-50 and GP II$_b$ III$_a$ affinity chromatography as described in Example B. Final resolution of the isoforms was accomplished by C-18 reverse phase HPLC (FIG. 8). Activity assays of the HPLC fractions using the Fg/GP II$_b$ III$_a$ ELISA revealed over 10 active fractions; the five fractions containing the most activity were designated ornatin A, B, C, D, and E, and were further characterized. Ornatin A was further resolved into 3 additional active components by rechromatography using a shallower initial gradient (FIG. 8). Purification data for the isolation of the ornatin isoforms are summarized in Table III, which denotes total units. Total units are defined as the dilution required to give a half maximal response in the fibrinogen/GP II$_b$ III$_a$ ELISA (described in the methods section) multiplied by the total volume in ml., specific activity, and recovery following each purification step.

TABLE III

Recovery of ornatin isoforms from 310 g of *P. ornata*

| fraction | volume (ml) | protein conc.[a] (mg/ml) | total protein (mg) | half maximal dilution | total units[b] | % recovery | specific activity (U/mg) |
|---|---|---|---|---|---|---|---|
| crude | 975 | 27.5[c] | 26813 | 98 | 95550 | 100 | 3.6 |
| TCA supernat. | 110 | 4.1[c] | 451 | 428 | 47080 | 49 | 104.4 |
| G-50 pool | 585 | 0.046 | 27 | 54 | 31590 | 33 | 1170 |
| affinity eluate | 47 | | | 315 | 14805 | 16 | |
| ornatin A2 | 0.5 | 0.018 | 0.0091 | 809 | 405 | 0.4 | 44505 |
| ornatin B | 0.5 | 0.024 | 0.0120 | 1215 | 608 | 0.6 | 50670 |
| ornatin C | 0.5 | 0.113 | 0.0566 | 4422 | 2211 | 2.3 | 39060 |
| ornatin D | 0.5 | 0.020 | 0.0104 | 1032 | 516 | 0.5 | 49615 |

TABLE III-continued

Recovery of ornatin isoforms from 310 g of P. ornata

| fraction | volume (ml) | protein conc.[a] (mg/ml) | total protein (mg) | half maximal dilution | total units[b] | % recovery | specific activity (U/mg) |
|---|---|---|---|---|---|---|---|
| ornatin E | 0.5 | 0.085 | 0.0426 | 3610 | 1805 | 1.9 | 42370 |

[a]Determined by amino acid composition.
[b]Total units is defined as the dilution required to give a half maximal response in the Fg/GP II$_b$ III$_a$ ELISA multiplied by the total volume in ml of the fraction.
[c]Determined by the method of Bradford (Bradford, M. M. (1976) Anal. Biochem. 72, 248-254).

Initial screening of crude homogenates from several different types of leeches indicated that the *P. ornata* homogenate showed a high level of total activity as well as a high level of activity when normalized to protein concentration relative to other leech homogenates. The existence of several isoforms of ornatin which differ in amino acid sequence stands in contrast to decorsin, a similar GP II$_b$ III$_a$ antagonist isolated from the leech *Macrobdella decora* (Seymour, J. L., Henzel, W. J., Nevins, B., Stults, J. T., and Lazarus, R. A. (1990) *J. Biol. Chem.* 265, 10143-10147). In the isolation of decorsin only 2 isoforms were identified and purified, one being an N-3 isoform, the other an N-2 isoform, lacking the first 3 or 2 N-terminal residues, respectively; no amino acid substitutions were found. The existence of such isoforms has, however, been noted in the family of GP II$_b$ III$_a$ antagonists isolated from snake venoms (Dennis, M. S., Henzel, W. J., Pitti, R. M., Lipari, M. T., Napier, M. A., Deisher, T. A., Bunting, S.; and Lazarus, R. A. (1990) *Proc. Natl. Acad. Sci. USA*, 87, 2471-2475).

Molecular Weight and Mass Spectrometry

Purified ornatin isoforms (C, D, E) were analyzed by electrophoresis on 20% SDS-polyacrylamide gels in the presence of dithiothreitol followed by silver staining and revealed single protein bands at a molecular weight <6,200 daltons. Fast atom bombardment (FAB) mass spectra were obtained with a JEOL HX110HF/HX110HF tandem double-focusing mass spectrometer, using MS-1 only. The instrument was operated at 10 kV accelerating voltage, 500 resolution, and the mass axis was scanned from 100 to 5000 u in 1 minute. The JEOL cesium gun was operated at 2.2 A filament current to produce 15 keV cesium ions. Data were acquired as single scans using the ACM program of the JEOL DA-5000 data system. A summary of the molecular weights obtained from mass spectral data is shown in Table IV.

TABLE IV

FAB-MS data of ornatin isoforms

| isoform | molecular mass (amu) observed[a] | calculated[b] |
|---|---|---|
| ornatin A2 | 4449.6 (1) | 4449.0 |
| ornatin B | 5868.2 (2) | 5866.6 |
| ornatin C | 5839.5 (2) | 5838.7 |
| ornatin D | 5721.6 (2) | — |
| ornatin E | 5722.5 (4) | 5721.5 |

[a]Data are corrected for the ionized M + 1 (H$^+$) peak that is observed; the observed molecular mass is the average of the number of determinations indicated in parenthesis.
[b]The calculated molecular masses were determined from the sequence of the native proteins, assuming that all cysteines form disulfide bonds.

The observed masses were reproducible within 2 amu and were found to be within 2 amu of the calculated mass from the amino acid sequence, based on the assumption that the 6 cysteines are present as disulfide bonds in the native protein.

Amino Acid Sequence and Composition Analysis

The complete amino acid sequence of ornatin isoforms A2, B, C, and E were determined as follows. First, the N-terminal half of the native protein sequences were obtained by subjecting the isoforms to sequential Edman degradation by loading an aliquot of purified isoform (ca. 100 pmol) onto a model 470A Applied Biosystems gas phase sequencer equipped with a 120A PTH amino acid analyzer. The complete sequence of ornatinA2 and the partial sequence of ornatinD were obtained by this method. PTH amino acid peaks were integrated with a Nelson Analytical model 3000 data system; data analysis was performed on a Vax 6850 Digital Equipment System according to the method of Henzel et. al. (Henzel, W. J., Rodrigues, H., and Watanabe, C. (1987) J. Chromatogr. 404, 41-52).

Next, aliquots of the purified isoforms (ca 400-800 pmol) were subjected to digestion with the endoprotease Asp-N, followed directly by sequencing or by reduction and carboxymethylation. The resulting alkylated fragments were purified by HPLC and replicate sequenced as before to obtain the C-terminal half of the isoform sequences. The conditions for Asp-N digestion were as follows: native ornatin was incubated with the protease at a 1/10 ratio (w/w, protease/ornatin) in 50-100 mM ammonium bicarbonate, at 37° C. for 12-18 hours. The conditions for reduction and carboxymethylation were as follows: the Asp-N reaction mixture was vacuum evaporated to dryness and redissolved in ca. 60 ul 6.5M guanidine hydrochloride, 100 mM Tris-HCl, pH 8.0, and reduced by the addition of 10% by volume tributylphosphine/1-propanol (1% v/v) at 37° C. for 2 hours. Alkylation was effected by the addition of 10 ul of 100 mM iodoacetic acid in 1M sodium hydroxide followed by incubation at 20° C. for 20 minutes in the dark. HPLC purification of ornatin fragments was performed using 100×2.1 mm SynChropak C-18, C-8, or C-4 reverse phase columns equilibrated in 0.1% TFA and eluted with linear gradients of 0 to 70% acetonitrile/0.08% TFA or 1-propanol/0.08% TFA. Absorbance was monitored at 214 and 280 nanometers; fractions were collected manually. The sequence of these fragments was then determined as described above. In this manner, the complete amino acid sequences of ornatin isoforms B, C, and E were determined. These sequences are illustrated in FIG. 9.

Amino acid compositions of the ornatin isoforms were determined as follows: protein samples (ca 100 pmol) were hydrolyzed under vacuum with constant boiling 6N HCl vapor in the Millipore Picotag system for 20 hours at 110° C. The hydrolysates were vacuum evaporated in a Savant speed vac concentrator, and analyzed on a Beckman model 6300 amino acid analyzer equipped with a ninhydrin detector. The amino acid compositions of the ornatin isoforms are shown in Table V.

TABLE V

Amino Acid Composition of Ornatin Isoforms

| Amino acid | Ornatin A2 | Ornatin B | Ornatin C | Ornatin D | Ornatin E |
|---|---|---|---|---|---|
| Asp | 7.03 (8)[a] | 9.10 (10) | 5.83 (6) | 7.64 | 7.77 (8) |
| Thr | 2.43 (3) | 2.20 (2) | 3.08 (3) | 1.99 | 2.54 (2) |
| Ser | 1.03 (1) | 1.19 (1) | 1.16 (1) | 0.70 | 0.00 (0) |
| Glu | 2.80 (3) | 3.02 (3) | 4.14 (4) | 3.78 | 4.00 (4) |
| Gly | 3.72 (4) | 4.53 (5) | 5.23 (5) | 4.76 | 4.96 (5) |
| Ala | 1.21 (1) | 2.16 (2) | 3.15 (3) | 1.25 | 1.43 (1) |
| Cys | 2.53 (6) | 2.58 (6) | 0.00 (6) | 3.76 | 3.11 (6) |
| Val | 1.55 (2) | 1.80 (2) | 2.00 (2) | 1.71 | 1.78 (2) |
| Met | 0.00 (0) | 0.09 (0) | 0.00 (0) | 0.17 | 0.00 (0) |
| Ile | 1.58 (2) | 1.50 (2) | 1.08 (1) | 1.59 | 1.90 (2) |
| Leu | 0.00 (0) | 1.93 (2) | 3.31 (3) | 2.51 | 2.94 (3) |
| Tyr | 0.00 (0) | 2.07 (2) | 1.97 (2) | 1.85 | 2.04 (2) |
| Phe | 0.00 (0) | 1.98 (2) | 2.01 (2) | 2.03 | 2.00 (2) |
| His | 0.34 (0) | 0.09 (0) | 0.53 (0) | 0.04 | 0.36 (0) |
| Lys | 4.37 (5) | 4.77 (5) | 5.75 (6) | 4.26 | 4.66 (5) |
| Arg | 2.70 (3) | 4.77 (5) | 5.12 (5) | 5.01 | 5.31 (5) |
| Pro | 2.93 (3) | 3.55 (3) | 2.58 (3) | 3.65 | 3.41 (3) |

[a]The values in parentheses represent the number of residues calculated from the amino acid sequence.

The molecular masses determined by FAB-MS analysis of the native proteins (Table IV) were consistent with the complete amino acid sequences obtained from Edman degradation for isoforms A2, B, C, and E, and verified that the complete sequences had been determined. Ornatin isoforms A2, B, C, and E each contain 6 cysteine residues, the placement of which is conserved, along with the Arg-Gly-Asp (RGD) tripeptide sequence. Isoform A2 exhibits the highest level of sequence heterogeneity relative to the other isoforms, and also appears to lack the first 9 residues of the N-terminus compared to the other isoforms.

EXAMPLE K

Inhibition of GP II$_b$ III$_a$/fibrinogen binding and platelet aggregation

The activity of the ornatin isoforms and several controls was measured for inhibition of GP II$_b$ III$_a$/fibrinogen binding and platelet aggregation as described previously for decorsin in examples F and G. The results are tabulated in Table VI.

TABLE VI

GP II$_b$ III$_a$ antagonist activity data

| compound | IC$_{50}$ (nM) Fg/GP IIb-IIIa solid phase ELISA | human platelet aggregation assay[a] |
|---|---|---|
| ornatin A2 | 5.1 (1)[b] | — |
| ornatin B | 3.5 ± 0.25 (3) | — |
| ornatin C | 4.9 ± 0.50 (4) | 324 (1) |
| ornatin D | 3.2 ± 0.35 (3) | — |
| ornatin E | 4.5 ± 0.77 (4) | 516 (1) |
| kistrin | 4.6 ± 0.06 (3) | 137 (1) |
| decorsin | — | 314 ± 56 (2) |
| GRGDV | 47.5 ± 6.4 (2) | — |

[a]Values are reported for ADP activation.
[b]The numbers in parenthesis refer to the number of independent determinations.

EXAMPLE L

Production and Purification of Recombinant Ornatin

A synthetic gene for one of the ornatin isoforms, (ornE) encoding ornatinE, a leech derived platelet aggregation inhibitor and GP II$_b$ III$_a$ antagonist, was designed, constructed, and ligated into plasmid pBO475 (Cunningham, B. C. et al., (1989) Science 243, 1330–1336; Cunningham, B. C.; and Wells, J. A. (1989) Science, 244, 1081–1085, Wells, J. and Cunningham, B., co-pending application U.S. Ser. No. 07/428,066, filed Oct. 26, 1989) in order to express the protein in E. coli. This construction creates a fusion between the ornatin gene and the stII (heat-stable enterotoxin) signal sequence, which directs the secretion of the gene product into the periplasmic space, and gives proper alignment for cleavage by signal peptidase (Chang, C. N.; Rey, M.; Bochner, B.; Heyneker, H.; and Gray, G. (1987) Gene, 55, 189–196.). The fusion gene is under the control of the E. coli alkaline phosphatase transcriptional promoter. The plasmid also contains the pMB1 origin of replication, and the f1 origin of replication, which permits production of single stranded DNA with the aid of coinfection of K07 helper phage. Expression of the ornatin gene is effected by transformation of E. coli (or other suitable bacteria) with the ornatin expression plasmid, selection of transformants, and growth of the transformants in suitable media. Recombinant ornatin can be recovered from cultures of such transformants, and purified by a variety of methods.

Materials

All restriction enzymes were purchased from New England Biolabs or Bethesda Research Laboratories (BRL). T4 DNA ligase and T4 DNA kinase were purchased from BRL, and T7 DNA polymerase was purchased from Pharmacia. All enzymes were used according to the recommendations of the supplier. Oligonucleotides were synthesized using hydrogen phosphonate chemistry (Froehler, B. C.; Ng, P. G.; and Matteuci, M. D. (1986) Nucleic Acids Res., 14, 5399–5407.), and purified by polyacrylamide gel electrophoresis.

Construction of the synthetic gene

Protocol for all DNA manipulations essentially followed those described in Molecular Cloning (Sambrook, J.; Fritsch, E. F.; and Maniatis, T., Molecular Cloning, second edition, Cold Spring Harbor Laboratory Press (1989)). The ornatin gene is assembled from 6 synthetic oligonucleotides, 56 to 64 base pairs in length, each sharing a unique 4 base pair overlap with the neighboring oligonucleotide, and the 5' and 3' terminii constructed to accommodate nsiI and styI sticky ends, respectively (FIG. 10). The synthetic oligonucleotides were phosphorylated individually, and annealed together in pairs by gradual cooling from 85° C. to 20° C.

Construction of the ornE expression plasmid and DNA sequencing

Although the description herein refers to the ornatinE isoform, it is understood that any of the isoforms may be produced recombinantly using these procedures. The double stranded DNA segments formed after annealing were ligated together with the 3.9 kb fragment of pBO475 which has been isolated after restriction digestion with NsiI and StyI. (FIG. 11). pBO475 contains the alkaline phosphatase promoter, followed by the stII signal and the gene encoding human growth hormone on and NsiI-BglII fragment, as well as the bacteriophage f1 and pMB1 origins of replication and the ampicillin resistance gene (Cunningham, B. C. et al., ibid). Only the styI restriction site is maintained in this construction; the N-terminal isoleucine of ornatinE prevents the retention of the nsiI restriction site. This construction is referred to as pOrnE. The pOrnE plasmid was then transformed in *E. coli* strain JM101 (or another suitable *E. coli* strain) and plated on LB agar containing 50 μg/ml carbenicillin. DNA from several of the carbenicillin resistant colonies is isolated using standard miniprep procedures (Sambrook, J. et al., ibid), and was then subjected to restriction analysis. Single stranded template DNA was obtained from those clones which appear to contain the correct insert size by purification from K07 helper phage infected cultures (Viera, J.; and Messing, J., (1987) *Methods Enzymol.* 153, 3-11). The single stranded DNA was then sequenced according to standard protocols (Sanger, F., Nicklen, S., and A. R. Coulsen, (1977) *Proc. Natl. Acad. Sci., USA* 74, 5463-5467).

Expression of the ornE synthetic gene.

Clones containing the correct DNA sequence encoding the ornatinE gene were inoculated into culture media and grown at 37° C. for 16 hours on a rotary shaker. Any of several media may be used, for example, rich media such as LB or 2YT, or minimal media, such as AP5 (AP5 contains (per liter): 3 ml 50% glucose, 2.2 g casamino acids, 0.3 g yeast extract, 1.6 ml 1M magnesium sulfate, 1.07 g ammonium chloride, 0.075 g potassium chloride, 70 ml 1M sodium chloride, and 120 ml 1M triethanolamine, pH 7.4). Rich media has the advantage of allowing high cell density due to the abundance of nutrients; minimal media has the advantage of inducing higher expression levels, since the low level of phosphate causes the alkaline phosphatase promoter to increase expression. These advantages can be combined by first growing the bacteria overnight in rich media, pelleting the cells by centrifugation, and resuspending in minimal media. The resuspended cells are incubated at 37° C. on a rotary shaker for 8 to 16 hours. This combined media approach results in a higher recovery of ornatinE than growth in either media alone.

Recovery and Purification of Recombinant Ornatin

The bacterial cultures are grown as described above and the recombinant ornatin is recovered as follows. The cells are harvested by centrifugation and frozen at −20° C. for 1 hour, then subjected to osmotic shock by resuspension in 10 mM Tris-HCl, pH 7.5 with magnetic stirring at 4° C. for 1 hour. The suspension is centrifuged, and the supernatant (referred to as the shockate) which contains the recombinant ornatin, is then used as the starting material for further purification. The ornatin may be purified using the purification scheme described herein for the isolation of ornatin from *P. ornata* leeches; alternatively, ornatin may be purified from the shockate by TFA precipitation followed by a sizing step (for example, molecular exclusion chromatography or filtration through an Amicon YM10 membrane), ion exchange chromatography, and finally by chromatography on C18 reversed phase HPLC under the conditions described herein.

---

What is claimed is:

1. A composition of matter comprising a purified polypeptide having an amino acid sequence selected from the group (Seq. ID Nos. 6, 7, 8, 9, 10, 16, 17, 18, 19, and 21)

PPGOCRFPRGDADPY,

TVGKCTIARGDDNDK,

TVGRCKFARGDNDDK,

TVGRCKFARGDADDK,

TVGRCNFARGDNDDK,

APRLPQCQGDDQEKCLCNK-
DECPPGQCRFPRGDADPYCE,

IPQCRDVKESGQPNDKCRCNGKPCTVGK-
CTIARGDDNDKCT,

IYVRPTNDELNYCGD-
FRELGQPDKKCRCDGKPCTVGRC-
KFARGDNDDKCISA,

IYVRPTKDELLYCGE-
FRELGQPDKKCRCDGKPCTVGRC-
KFARGDADDKCTSA, and

IYVRPTKDELLYCGE-
FRELGQPDKKCRCDGKPCTVGRCN-
FARGDNDDKCI.

2. A composition of matter comprising a purified polypeptide having an amino acid sequence selected from the group ornatinA2, ornatinB, ornatinC, ornatinD, ornatinE and mixtures thereof.

3. A composition of matter comprising a purified polypeptide having an amino acid sequence of decorsin.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( D ) TOPOLOGY: linear ( x i ) SEQUENCE DESCRIPTION: SEQ ID NO:1:

Arg Phe Pro Arg Gly Asp Ala Asp Pro Tyr
 1               5                   10

( 2 ) INFORMATION FOR SEQ ID NO:2:

( i ) SEQUENCE CHARACTERISTICS:
      ( A ) LENGTH: 10 amino acids
      ( B ) TYPE: amino acid
      ( D ) TOPOLOGY: linear ( x i ) SEQUENCE DESCRIPTION: SEQ ID NO:2:

Thr Ile Ala Arg Gly Asp Asp Asn Asp Lys
 1               5                   10

( 2 ) INFORMATION FOR SEQ ID NO:3:

( i ) SEQUENCE CHARACTERISTICS:
      ( A ) LENGTH: 10 amino acids
      ( B ) TYPE: amino acid
      ( D ) TOPOLOGY: linear ( x i ) SEQUENCE DESCRIPTION: SEQ ID NO:3:

Lys Phe Ala Arg Gly Asp Asn Asp Asp Lys
 1               5                   10

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:4:

```
Lys Phe Ala Arg Gly Asp Ala Asp Asp Lys
 1               5                  10
```

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:5:

```
Asn Phe Ala Arg Gly Asp Asn Asp Asp Lys
 1               5                  10
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:6:

```
Pro Pro Gly Gln Cys Arg Phe Pro Arg Gly Asp Ala Asp Pro Tyr
 1               5                  10                  15
```

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:7:

```
Thr Val Gly Lys Cys Thr Ile Ala Arg Gly Asp Asp Asn Asp Lys
 1               5                  10                  15
```

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:8:

```
Thr Val Gly Arg Cys Lys Phe Ala Arg Gly Asp Asn Asp Asp Lys
 1               5                  10                  15
```

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:9:

```
Thr Val Gly Arg Cys Lys Phe Ala Arg Gly Asp Ala Asp Asp Lys
 1               5                  10                  15
```

(2) INFORMATION FOR SEQ ID NO:10:

(i) SEQUENCE CHARACTERISTICS:
        (A) LENGTH: 15 amino acids (B) TYPE: amino acid
(D) TOPOLOGY: linear (xi) SEQUENCE DESCRIPTION: SEQ ID NO:10:

Thr Val Gly Arg Cys Asn Phe Ala Arg Gly Asp Asn Asp Asp Lys
 1               5                  10                  15

(2) INFORMATION FOR SEQ ID NO:11:

(i) SEQUENCE CHARACTERISTICS:
       (A) LENGTH: 12 amino acids
       (B) TYPE: amino acid
       (D) TOPOLOGY: linear (xi) SEQUENCE DESCRIPTION: SEQ ID NO:11:

Cys Xaa Xaa Xaa Arg Gly Asp Xaa Xaa Xaa Xaa Cys
 1               5                  10      12

(2) INFORMATION FOR SEQ ID NO:12:

(i) SEQUENCE CHARACTERISTICS:
       (A) LENGTH: 17 amino acids
       (B) TYPE: amino acid
       (D) TOPOLOGY: linear (xi) SEQUENCE DESCRIPTION: SEQ ID NO:12:

Cys Xaa Xaa Xaa Xaa Cys Xaa Xaa Xaa Arg Gly Asp Xaa Xaa Xaa
 1               5                  10                  15

Xaa Cys
    17

(2) INFORMATION FOR SEQ ID NO:13:

(i) SEQUENCE CHARACTERISTICS:
       (A) LENGTH: 22 amino acids
       (B) TYPE: amino acid
       (D) TOPOLOGY: linear (xi) SEQUENCE DESCRIPTION: SEQ ID NO:13:

Cys Xaa Xaa Xaa Xaa Cys Xaa Xaa Xaa Xaa Cys Xaa Xaa Xaa Arg
 1               5                  10                  15

Gly Asp Xaa Xaa Xaa Xaa Cys
            20          22

(2) INFORMATION FOR SEQ ID NO:14:

(i) SEQUENCE CHARACTERISTICS:
       (A) LENGTH: 24 amino acids
       (B) TYPE: amino acid
       (D) TOPOLOGY: linear (xi) SEQUENCE DESCRIPTION: SEQ ID NO:14:

Cys Xaa Cys Xaa Xaa Xaa Xaa Cys Xaa Xaa Xaa Xaa Cys Xaa Xaa
 1               5                  10                  15

Xaa Arg Gly Asp Xaa Xaa Xaa Xaa Cys
                20              24

(2) INFORMATION FOR SEQ ID NO:15:

(i) SEQUENCE CHARACTERISTICS:
       (A) LENGTH: 32 amino acids
       (B) TYPE: amino acid
       (D) TOPOLOGY: linear (xi) SEQUENCE DESCRIPTION: SEQ ID NO:15:

Cys Xaa Xaa Xaa Xaa Xaa Xaa Xaa Cys Xaa Cys Xaa Xaa Xaa Xaa
 1               5                  10                  15

```
Cys  Xaa  Xaa  Xaa  Xaa  Cys  Xaa  Xaa  Xaa  Arg  Gly  Asp  Xaa  Xaa  Xaa
               20                      25                           30

Xaa  Cys
     32
```

( 2 ) INFORMATION FOR SEQ ID NO:16:

( i ) SEQUENCE CHARACTERISTICS:
        ( A ) LENGTH: 39 amino acids
        ( B ) TYPE: amino acid
        ( D ) TOPOLOGY: linear ( x i ) SEQUENCE DESCRIPTION: SEQ ID NO:16:

```
Ala  Pro  Arg  Leu  Pro  Gln  Cys  Gln  Gly  Asp  Asp  Gln  Glu  Lys  Cys
 1              5                        10                          15

Leu  Cys  Asn  Lys  Asp  Glu  Cys  Pro  Pro  Gly  Gln  Cys  Arg  Phe  Pro
               20                      25                           30

Arg  Gly  Asp  Ala  Asp  Pro  Tyr  Cys  Glu
               35                      39
```

( 2 ) INFORMATION FOR SEQ ID NO:17:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:17:

```
Ile  Pro  Gln  Cys  Arg  Asp  Val  Lys  Glu  Ser  Gly  Gln  Pro  Asn  Asp
 1              5                        10                          15

Lys  Cys  Arg  Cys  Asn  Gly  Lys  Pro  Cys  Thr  Val  Gly  Lys  Cys  Thr
               20                      25                           30

Ile  Ala  Arg  Gly  Asp  Asp  Asn  Asp  Lys  Cys  Thr
               35                      40   41
```

( 2 ) INFORMATION FOR SEQ ID NO:18:

( i ) SEQUENCE CHARACTERISTICS:
        ( A ) LENGTH: 52 amino acids
        ( B ) TYPE: amino acid
        ( D ) TOPOLOGY: linear ( x i ) SEQUENCE DESCRIPTION: SEQ ID NO:18:

```
Ile  Tyr  Val  Arg  Pro  Thr  Asn  Asp  Glu  Leu  Asn  Tyr  Cys  Gly  Asp
 1              5                        10                          15

Phe  Arg  Glu  Leu  Gly  Gln  Pro  Asp  Lys  Lys  Cys  Arg  Cys  Asp  Gly
               20                      25                           30

Lys  Pro  Cys  Thr  Val  Gly  Arg  Cys  Lys  Phe  Ala  Arg  Gly  Asp  Asn
               35                      40                           45

Asp  Asp  Lys  Cys  Ile  Ser  Ala
               50        52
```

( 2 ) INFORMATION FOR SEQ ID NO:19:

( i ) SEQUENCE CHARACTERISTICS:
        ( A ) LENGTH: 52 amino acids
        ( B ) TYPE: amino acids
        ( D ) TOPOLOGY: linear ( x i ) SEQUENCE DESCRIPTION: SEQ ID NO:19:

```
Ile  Tyr  Val  Arg  Pro  Thr  Lys  Asp  Glu  Leu  Leu  Tyr  Cys  Gly  Glu
 1              5                        10                          15

Phe  Arg  Glu  Leu  Gly  Gln  Pro  Asp  Lys  Lys  Cys  Arg  Cys  Asp  Gly
               20                      25                           30
```

```
Lys Pro Cys Thr Val Gly Arg Cys Lys Phe Ala Arg Gly Asp Ala
             35                  40                  45

Asp Asp Lys Cys Thr Ser Ala
             50          52
```

( 2 ) INFORMATION FOR SEQ ID NO:20:

( i ) SEQUENCE CHARACTERISTICS:
        ( A ) LENGTH: 28 amino acids
        ( B ) TYPE: amino acid
        ( D ) TOPOLOGY: linear ( x i ) SEQUENCE DESCRIPTION: SEQ ID NO:20:

```
Ile Tyr Val Arg Pro Thr Lys Asp Glu Leu Leu Tyr Cys Gly Glu
 1               5                  10                  15

Phe Arg Glu Leu Gly Gln Pro Asp Lys Lys Cys Arg Cys
             20                  25          28
```

( 2 ) INFORMATION FOR SEQ ID NO:21:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:21:

```
Ile Tyr Val Arg Pro Thr Lys Asp Glu Leu Leu Tyr Cys Gly Glu
 1               5                  10                  15

Phe Arg Glu Leu Gly Gln Pro Asp Lys Lys Cys Arg Cys Asp Gly
             20                  25                  30

Lys Pro Cys Thr Val Gly Arg Cys Asn Phe Ala Arg Gly Asp Asn
             35                  40                  45

Asp Asp Lys Cys Ile
             50
```

( 2 ) INFORMATION FOR SEQ ID NO:22:

( i ) SEQUENCE CHARACTERISTICS:
        ( A ) LENGTH: 49 amino acids
        ( B ) TYPE: amino acid
        ( D ) TOPOLOGY: linear ( x i ) SEQUENCE DESCRIPTION: SEQ ID NO:22:

```
Glu Cys Glu Ser Gly Pro Cys Cys Arg Asn Cys Lys Phe Leu Lys
 1               5                  10                  15

Glu Gly Thr Ile Cys Lys Arg Ala Arg Gly Asp Asp Met Asp Asp
             20                  25                  30

Tyr Cys Asn Gly Lys Thr Cys Asp Cys Pro Arg Asn Pro His Lys
             35                  40                  45

Gly Pro Ala Thr
             49
```

( 2 ) INFORMATION FOR SEQ ID NO:23:

( i ) SEQUENCE CHARACTERISTICS:
        ( A ) LENGTH: 72 amino acids
        ( B ) TYPE: amino acid
        ( D ) TOPOLOGY: linear ( x i ) SEQUENCE DESCRIPTION: SEQ ID NO:23:

```
Glu Ala Gly Glu Asp Cys Asp Cys Gly Ser Pro Ala Asn Pro Cys
 1               5                  10                  15

Cys Asp Ala Ala Thr Cys Lys Leu Ile Pro Gly Ala Gln Cys Gly
             20                  25                  30
```

```
Glu Gly Leu Cys Cys Asp Gln Cys Ser Phe Ile Glu Glu Gly Thr
                35                  40                  45

Val Cys Arg Ile Ala Arg Gly Asp Asp Leu Asp Asp Tyr Cys Asn
                50                  55                  60

Gly Arg Ser Ala Gly Cys Pro Arg Asn Pro Phe His
                65                  70      72
```

( 2 ) INFORMATION FOR SEQ ID NO:24:

( i ) SEQUENCE CHARACTERISTICS:
        ( A ) LENGTH: 71 amino acids
        ( B ) TYPE: amino acid
        ( D ) TOPOLOGY: linear ( x i ) SEQUENCE DESCRIPTION: SEQ ID NO:24:

```
Glu Ala Gly Glu Glu Cys Asp Cys Glu Ser Pro Glu Asn Pro Cys
 1               5                  10                  15

Cys Asp Ala Ala Thr Cys Lys Leu Arg Pro Gly Ala Gln Cys Ala
                20                  25                  30

Glu Gly Leu Cys Cys Asp Gln Cys Lys Phe Met Lys Glu Gly Thr
                35                  40                  45

Val Cys Arg Ala Arg Gly Asp Asp Val Asn Asp Tyr Cys Asn Gly
                50                  55                  60

Ile Ser Ala Gly Cys Pro Arg Asn Pro Phe His
                65                  70  71
```

( 2 ) INFORMATION FOR SEQ ID NO:25:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:25:

```
Gly Lys Glu Cys Asp Cys Ser Ser Pro Glu Asn Pro Cys Cys Asp
 1               5                  10                  15

Ala Ala Thr Cys Lys Leu Arg Pro Gly Ala Gln Cys Gly Glu Gly
                20                  25                  30

Leu Cys Cys Glu Gln Cys Lys Phe Ser Arg Ala Gly Lys Ile Cys
                35                  40                  45

Arg Ile Pro Arg Gly Asp Met Pro Asp Asp Arg Cys Thr Gly Gln
                50                  55                  60

Ser Ala Asp Cys Pro Arg Tyr His
                65              68
```

( 2 ) INFORMATION FOR SEQ ID NO:26:

( i ) SEQUENCE CHARACTERISTICS:
        ( A ) LENGTH: 193 bases
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
AATTC   CCG GGA ATC GAA GGT CGT GCG CCG CGG CTG CCG   38
        Pro Gly Ile Glu Gly Arg Ala Pro Arg Leu Pro
         1               5                      10

CAG TGC CAA GGT GAC GAT CAG GAA AAA TGT CTG TGC AAC   77
Gln Cys Gln Gly Asp Asp Gln Glu Lys Cys Leu Cys Asn
                15                  20

AAA GAT GAA TGT CCC CCG GGT CAG TGT CGT TTC CCT CGA   116
Lys Asp Glu Cys Pro Pro Gly Gln Cys Arg Phe Pro Arg
 25                  30                  35
```

```
        GGT GAT GCG GAT CCG TAT TGT GAA    TAAGCATGCG TCGACTCTAG  160
        Gly Asp Ala Asp Pro Tyr Cys Glu
                40                  45

AGGGCCCAAA GCTTCTGCAC CCGGGTTTCG AAG  193
```

( 2 ) INFORMATION FOR SEQ ID NO:27:

( i ) SEQUENCE CHARACTERISTICS:
        ( A ) LENGTH: 121 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
        GCG CCG CGG CTG CCG CAG TGC CAA GGT GAC GAT CAG  36
        Ala Pro Arg Leu Pro Gln Cys Gln Gly Asp Asp Gln
         1               5                   10

GAA AAA TGT CTG TGC AAC AAA GAT GAA TGT CCC CCG GGT  75
        Glu Lys Cys Leu Cys Asn Lys Asp Glu Cys Pro Pro Gly
                 15                  20                  25

CAG TGT CGT TTC CCT CGA GGT GAT GCG GAT CCG TAT TGT  114
        Gln Cys Arg Phe Pro Arg Gly Asp Ala Asp Pro Tyr Cys
                     30                  35

GAA TAA A  121
        Glu
        39
```

( 2 ) INFORMATION FOR SEQ ID NO:28:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:28:

```
Cys Xaa Xaa Ala Arg Gly Asp Xaa Asp Asp Lys Cys
 1           5                   10      12
```

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:29:

```
Cys Xaa Xaa Pro Arg Gly Asp Xaa Asp Asp Lys Cys
 1           5                   10      12
```

( 2 ) INFORMATION FOR SEQ ID NO:30:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:30:

```
Cys Thr Val Gly Xaa Cys Xaa Xaa Ala Arg Gly Asp Xaa Asp Asp
 1               5                   10                  15

Lys Cys
 17
```

( 2 ) INFORMATION FOR SEQ ID NO:31:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:31:

Cys Thr Val Gly Xaa Cys Xaa Xaa Pro Arg Gly Asp Xaa Asp Asp
1               5                   10                  15
Lys Cys
    17

( 2 ) INFORMATION FOR SEQ ID NO:32:

( i ) SEQUENCE CHARACTERISTICS:
( A ) LENGTH: 168 bases
( B ) TYPE: nucleic acid
( C ) STRANDEDNESS: single
( D ) TOPOLOGY: linear ( x i ) SEQUENCE DESCRIPTION: SEQ ID NO:32:

```
ATC TAT GTT CGT CCG ACC AAA GAT GAG CTC CTG TAT  36
Ile Tyr Val Arg Pro Thr Lys Asp Glu Leu Leu Tyr
 1               5                   10

TGT GGT GAA TTT CGC GAA CTG GGT CAG CCG GAT AAA AAA  75
Cys Gly Glu Phe Arg Glu Leu Gly Gln Pro Asp Lys Lys
         15                  20                  25

TGC CGT TGT GAT GGT AAA CCG TGT ACC GTT GGT CGT TGT 114
Cys Arg Cys Asp Gly Lys Pro Cys Thr Val Gly Arg Cys
                  30                      35

AAC TTC GCG CGC GGT GAT AAC GAT GAT AAA TGT ATC 150
Asn Phe Ala Arg Gly Asp Asn Asp Asp Lys Cys Ile
     40                  45                  50

TAATGAGCAT GCGGATCC 168
```

( 2 ) INFORMATION FOR SEQ ID NO:33:

( i ) SEQUENCE CHARACTERISTICS:
( A ) LENGTH: 13 amino acids
( B ) TYPE: amino acid
( D ) TOPOLOGY: linear ( x i ) SEQUENCE DESCRIPTION: SEQ ID NO:33:

Cys Xaa Xaa Xaa Arg Gly Asp Xaa Xaa Xaa Xaa Xaa Cys
1               5                   10              13

( 2 ) INFORMATION FOR SEQ ID NO:34:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:34:

Gly Arg Gly Asp Val
1               5